US011786542B2

(12) United States Patent
Ahmed et al.

(10) Patent No.: US 11,786,542 B2
(45) Date of Patent: Oct. 17, 2023

(54) METHODS FOR ENHANCING CYTOTOXIC CANCER THERAPY THROUGH MODULATION OF PURINE BIOSYNTHESIS PATHWAYS

(71) Applicant: NORTHWESTERN UNIVERSITY, Evanston, IL (US)

(72) Inventors: Atique U. Ahmed, Evanston, IL (US); Jack M. Shireman, Chicago, IL (US); Cheol H. Park, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/098,177

(22) Filed: Nov. 13, 2020

(65) Prior Publication Data
US 2021/0145855 A1    May 20, 2021

Related U.S. Application Data

(60) Provisional application No. 62/936,139, filed on Nov. 15, 2019.

(51) Int. Cl.
*A61K 31/7056*    (2006.01)
*A61K 31/343*    (2006.01)
*A61K 31/495*    (2006.01)

(52) U.S. Cl.
CPC ........ *A61K 31/7056* (2013.01); *A61K 31/343* (2013.01); *A61K 31/495* (2013.01)

(58) Field of Classification Search
CPC . A61K 31/7056; A61K 31/343; A61K 31/495
USPC ........................................................ 514/43
See application file for complete search history.

(56) References Cited

PUBLICATIONS

Volpin et al. Use of an anti-viral drug, Ribavirin, as an anti-glioblastoma therapeutic. Oncogene (2017) 36, 3037-3047. Published online Dec. 12, 2016. (Year: 2017).*
Shah et al. Newer human inosine 50-monophosphate dehydrogenase 2 (hIMPDH2) inhibitors as potential anticancer agents. Journal of Enzyme Inhibition and Medicinal Chemistry 2018, vol. 33, No. 1, 972-977. Published online: May 24, 2018. (Year: 2018).*
Allison AC, et al. Mycophenolate mofetil and its mechanisms of action. Immunopharmacology. 2000; 47(2-3): 85-118.
Annovazzi L, et al. Chemotherapeutic Drugs: DNA Damage and Repair in Glioblastoma. Cancers (Basel). 2017; 9 (6).
Barfeld SJ, et al. Myc-dependent purine biosynthesis affects nucleolar stress and therapy response in prostate cancer. Oncotarget. 2015; 6(14): 12587-602.
Bay SN, et al. Disruption of the ciliary GTPase Arl13b suppresses Sonic hedgehog overactivation and inhibits medulloblastoma formation. Proc Natl Acad Sci U S A. 2018; 115(7): 1570-5.
Ben-Sahra I, et al. mTORC1 induces purine synthesis through control of the mitochondrial tetrahydrofolate cycle. Science. 2016; 351(6274): 728-33.
Ben-Sahra I, et al. Stimulation of de novo pyrimidine synthesis by growth signaling through mTOR and S6K1. Science. 2013; 339(6125): 1323-8.
Berg JM TJ, et al. Purine Bases Can Be Synthesized de Novo or Recycled by Salvage Pathways. Biochemistry 5th edition. 2002 .; 5th edition: Section 25.2.
Braun-Sand SB, et al. Inosine monophosphate dehydrogenase as a target for antiviral, anticancer, antimicrobial and Immunosuppressive therapeutics. Future Med Chem. 2010; 2(1): 81-92.
Chen L, et al. Recent development of IMP dehydrogenase inhibitors for the treatment of cancer. Curr Opin Drug Discov Devel. 2007; 10(4): 403-12.
Dhande, I. S., et al. "Mycophenolate mofetil prevents cerebrovascular injury in stroke-prone spontaneously hypertensive rats." Physiological genomics 49.3 (2017): 132-140.
Dhankhar R, et al. Diagnostic significance of adenosine deaminase, uric acid and C-reactive protein levels in patients of head and neck carcinoma. Clin Lab. 2011; 57(9-10): 795-8.
Eugui EM, et al. Lymphocyte-selective antiproliferative and immunosuppressive effects of mycophenolic acid in mice. Scand J Immunol. 1991; 33(2): 175-83.
Garrido W, et al. Chemoresistance in high-grade gliomas: relevance of adenosine signalling in stem-like cells of glioblastoma multiforme. Curr Drug Targets. 2014; 15(10): 931-42.
Goswami MT, et al. Role and regulation of coordinately expressed de novo purine biosynthetic enzymes PPAT and PAICS in lung cancer. Oncotarget. 2015; 6(27): 23445-61.
Hedstrom L. IMP dehydrogenase: structure, mechanism, and inhibition. Chem Rev. 2009; 109(7): 2903-28.
Huang F, et al. Inosine Monophosphate Dehydrogenase Dependence in a Subset of Small Cell Lung Cancers. Cell Metab. 2018; 28(3): 369-82 e5.
Ishikawa, H. "Mizoribine and mycophenolate mofetil." Current medicinal chemistry 6 (1999): 575-598.
Jin X, et al. Targeting glioma stem cells through combined BMI1 and EZH2 inhibition. Nat Med. 2017; 23(11): 1352-61.
Nemkov T, et al. Hypoxia modulates the purine salvage pathway and decreases red blood cell and supernatant levels of hypoxanthine during refrigerated storage. Haematologica. 2018; 103(2): 361-72.
Pillwein K, et al. Purine metabolism of human glioblastoma in vivo. Cancer research. 1990; 50(5): 1576-9.
Rai B, et al. Adenosine deaminase in saliva as a diagnostic marker of squamous cell carcinoma of tongue. Clin Oral Investig. 2011; 15(3): 347-9.
Rodriguez-Pascual J, et al. A preclinical and clinical study of mycophenolate mofetil in pancreatic cancer. Invest New Drugs. 2013; 31(1): 14-9.

(Continued)

*Primary Examiner* — Yih-Horng Shiao
(74) *Attorney, Agent, or Firm* — QUARLES & BRADY LLP

(57) ABSTRACT

Disclosed are methods and compositions for treating proliferative cell diseases and disorders such as cancers. Particularly disclosed are methods and composition for treating cancers such as glioblastoma by administering a therapeutic agent that alters the pathways used for purine biosynthesis by inhibiting the biological activity of ARL13B and/or IMPDH proteins in conjunction with additional therapeutic agents such as alkylating agents.

8 Claims, 20 Drawing Sheets

(56) References Cited

PUBLICATIONS

Shireman, J., et al. "Ciliary Protein ARL13B Promotes Chemoresistance By Modulate Glioblastoma Purine Biosynthesis." American Association of Cancer Research Annual Meeting 2019 (Mar. 29-Apr. 3, 2019; Atlanta, GA).

Shireman, J., et al. "DRES-02. Ciliary Protein ARL13B Promotes Chemoresistance By Modulate Glioblastoma Purine Biosynthesis." Neuro-Oncology 20.Suppl 6 (2018): vi75.

Siebert A, et al. New Analogues of Mycophenolic Acid. Mini Rev Med Chem. 2017; 17(9): 734-45.

Takebe N, et al. Phase I clinical trial of the inosine monophosphate dehydrogenase inhibitor mycophenolate mofetil (cellcept) in advanced multiple myeloma patients. Clinical cancer research : an official journal of the American Association for Cancer Research. 2004; 10(24): 8301-8.

Vilpo JA, et al. Nucleoside monophosphate kinase may be the key enzyme preventing salvage of DNA 5-methylcytosine. Mutat Res. 1993; 286(2): 217-20.

Wang X, et al. Purine synthesis promotes maintenance of brain tumor initiating cells in glioma. Nat Neurosci. 2017; 20 (5): 661-73.

Yokota, S. "Mizoribine: mode of action and effects in clinical use." Pediatrics international 44.2 (2002): 196-198.

Zauri M, et al. CDA directs metabolism of epigenetic nucleosides revealing a therapeutic window in cancer. Nature. 2015; 524(7563): 114-8.

Zhu Z, et al. Mycophenolate mofetil improves neurological function and alters blood T-lymphocyte subsets in rats with experimental autoimmune encephalomyelitis. J Int Med Res. 2014; 42(2): 530-41.

Volpin et al. Use of an anti-viral drug, Ribavirin, as an anti-glioblastoma therapeutic. Oncogene (2017) 36, 3037-3047.

Shah et al. Newer human inosine 50-monophosphate dehydrogenase 2 (hIMPDH2) inhibitors as potential anticancer agents. Journal of Enzyme Inhibition and Medicinal Chemistry 2018, vol. 33, No. 1, 972-977.

\* cited by examiner

METHODS FOR ENHANCING CYTOTOXIC CANCER THERAPY THROUGH MODULATION OF PURINE BIOSYNTHESIS PATHWAYS

CROSS-REFERENCE TO RELATED PATENT APPLICATIONS

This invention claims priority under 35 U.S.C. § 119(e) to U.S. Provisional Application No. 62/936,139 filed on Nov. 15, 2019, the contents of which is incorporated by reference in its entirety.

BACKGROUND

The invention relates to methods for treating proliferative cell diseases and disorders such as cancers. In particular, the invention relates to methods for treating cancers such as glioblastoma by administering a therapeutic agent that inhibits the biological activity of ARL13B or IMDPH.

Only 3% of patients diagnosed with glioblastoma multiforme (GBM) survive longer than five years, making GBM one of the most lethal forms of human cancer. GBM is a remarkably adaptive form of brain cancer that even with an aggressive standard of care therapy claims thousands of lives every year. New treatments are desperately needed to extend the lives of these patients. The repurposing of already FDA approved drugs represents a critical way to deliver meaningful therapies to current patients rapidly and safely, especially when compared to the lengthy and costly process of drug discovery and development. We have discovered an exploitable facet of GBM purine biosynthesis that when targeted allows Temozolomide, the standard chemotherapeutic, to become radically more effective in controlling tumor size and growth in the animal models. This target is already druggable using FDA approved compounds and could be rapidly translatable to the clinic to provide benefit to patients. Our findings can be used to devise a new and effective treatment strategy for currently therapeutically resistant cancers such as glioblastoma, which could be available to patients as first line treatment or given to patients once therapeutic resistance to normal standard of care occurs. This new and effective treatment strategy can be rapidly deliverable to a patient population due to the use of already FDA-approved drugs (e.g., CellCept) or drugs in use for therapies in other countries (e.g., Mizoribine) to target GBM purine biosynthesis.

SUMMARY

Disclosed are methods and kits for treatment of proliferative cell diseases, including cancer, especially including glioblastoma multiforme (GBM) in a subject in need thereof. In some of the methods, a proliferative cell disease or disorder is treated by (i) administering to the subject a therapeutic agent that inhibits or reduces the biological activity of IMDPH1 or IMDPH2, and (ii) administering to the subject an alkylating agent. In some of the methods, a proliferative cell disease or disorder is treated by (i) administering to the subject a therapeutic agent that inhibits the expression and/or other biological activity of ALRL13B, and (ii) administering to the subject an alkylating agent.

The disclosed kits may combine an inhibitor of GBM purine synthesis together with an alkylating agent. In some embodiments, the disclosed kits may include a therapeutic agent that that inhibits or reduces biological activity of IMDPH1 or IMDPH2, and an alkylating agent. In other embodiments, the disclosed kits may include a therapeutic agent that inhibits the expression and/or other biological activity of ARL13B and an alkylating agent.

DETAILED DESCRIPTION

Figure 1A:
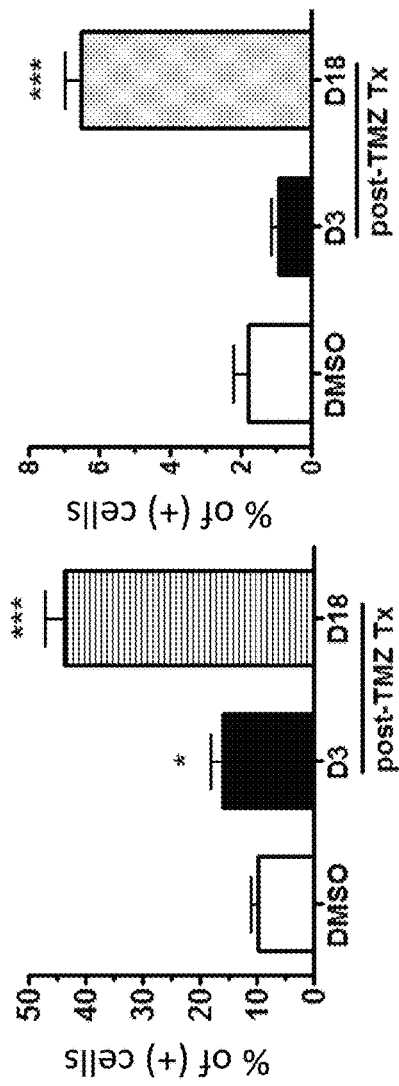
FIG. 1A-1D. ARL13B is a downstream target for EZH2 non-canonical function. A) EZH2 expression is elevated during (day 3-D3) and post (D18) TMZ therapy. Therapy resistant glioma stem cell (CD133+) express high EZH2 post therapy (left). B) EZH2 inhibitor (EZH2-I)+TMZ can block the tumor growth in vivo in the flank model. C) To examine the role of non-canonical function in TMZ resistance GBM43 (proneural) and GBM6 (Classical) PDX GBM treated with TMZ or TMZ+EZH2 inhibitor and subject to RNAseq analysis. The downregulated genes in TMZ+ EZH2 condition as compared to TMZ treatment were considered to be regulated by EZH2 non-canonical function. We identified ARL13B as the top hit from this screen. D) shRNA mediated knockdown of EZH2 leads to downregulation of ARL13B.

Disclosed are methods and compositions for treating, inhibiting, and/or preventing proliferative cell diseases. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient.

As used herein, the term "subject" and/or the term "subject in need thereof" is meant to encompass a person who has a proliferative cell disease or disorder, such as cancer, particularly a cancer that is treated by administering an alkylating agent to the person. A "subject" may include a subject who has cancer of the brain, such as glioblastoma multiforme (GBM) or astrocytoma. A "subject" also may include a subject who has a cancer of the breast, lung, liver, head & neck, colon, prostate, pancreas, stomach, or other types of cancer that are amenable to treatment with an alkylating agent.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "inhibit" means decreasing or blocking biological activity. For example, "inhibiting" may include reducing or blocking biological activity of the ARL13B protein. "Inhibiting" also may include reducing or blocking biological activity of the inosine-5' monophosphate dehydrogenase (IMPDH) protein.

The disclosed methods and compositions relate to treating proliferative cell diseases and disorders in a subject in need thereof. In some embodiments, the disclosed methods and compositions relate to treating a proliferative cell disease or disorder, such as glioblastoma multiforme (GBM), by administering a therapeutic agent that inhibits the biological activity of the ARL13B protein, and optionally, in conjunction, administering an additional therapeutic and/or alkylating agent or a treatment that treats the proliferative cell disease or disorder. In some embodiments, the disclosed methods and compositions relate to treating a proliferative cell disease or disorder, such as glioblastoma multiforme (GBM), by administering a therapeutic agent that inhibits the biological activity of the Inosine-5' monophosphate dehydrogenase (IMPDH) protein, including any of its isoforms, such as the IMPDH1 protein, the IMPDH2 protein, any other isoform of the IMPDH protein; and optionally, in conjunction, administering an additional therapeutic and/or alkylating agent or a treatment that treats the proliferative cell disease or disorder.

ARL13B is a member of the ADP-ribosylation factor-like family protein accountable for cilia maintenance. ARL13B is a small GTPase that contains both N- and C-terminal guanine nucleotide-binding motifs. This protein is localized in cilia and plays a role in their formation. Mutations in this gene are the cause of Joubert syndrome. Disruption of ARL13B inhibits cilia-dependent oncogenic sonic hedgehog signaling (SHH) in medulloblastoma. A recent report has demonstrated that GBM cells express cilia-like structures which were positive for ARL13B.

In a study performed by the inventors, ARL13B was the top gene whose expression was significantly downregulated in the presence of EZH2 inhibitors, being downregulated approximately 6-fold. ChIP-Seq analysis revealed that EZH2 binds within an enhancer site of ARL13B and this binding is effected by Temozolomide treatment. As such, the disclosed methods and kits may utilize or include one or more therapeutic agents that inhibit one or more biological activities of ARL13B.

In some embodiments, the disclosed methods and compositions relate to treating a proliferative cell disease or disorder in in a subject in need thereof by administering to the subject a therapeutic agent that comprises an alkylating agent. For example, in some embodiments, the disclosed methods and composition relate to treating a proliferative cell disease or disorder by administering to a subject in need thereof a therapeutic agent that inhibits the biological activity of ARL13B and administering to the subject an alkylating agent. The alkylating agent may be administered to the subject before, concurrently with, or after the therapeutic agent that inhibits the biological activity of ARL13B is administered to the subject. Suitable alkylating agents for the disclosed methods and compositions may include, but are not limited to, triazines (e.g., temozolomide, and decarbazine), ethylenimines (e.g., altretamine, and thiotepa), alky sulfonates (e.g., busulfan), nitrosoureas (e.g., carmustine, lomustine, and steptozocin), and nitrogen mustards (e.g., bendamustine, chlorambucil, cyclophosphamide, ifosfamide mechlorethamine, and melphalan).

In some embodiments, the disclosed methods and compositions relate to treating a proliferative cell disease or disorder in in a subject in need thereof by administering to the subject a therapeutic agent that inhibits the biological activity of IMPDH1, IMPDH2, another isoform of IMPDH, or any combination thereof. In some embodiments, the disclosed methods and composition relate to treating a proliferative cell disease or disorder by administering to a subject in need thereof a therapeutic agent that inhibits the biological activity of IMPDH1, IMPDH2, another isoform of IMPDH, or any combination thereof and administering to the subject an alkylating agent. The alkylating agent may be administered to the subject before, concurrently with, or after the therapeutic agent that inhibits the biological activity of IMPDH1, IMPDH2, another isoform of IMPDH, or any combination thereof is administered to the subject. Suitable alkylating agents for the disclosed methods and compositions may include, but are not limited to, triazines (e.g., temozolomide, and decarbazine), ethylenimines (e.g., altretamine, and thiotepa), alky sulfonates (e.g., busulfan), nitrosoureas (e.g., carmustine, lomustine, and steptozocin), and nitrogen mustards (e.g., bendamustine, chlorambucil, cyclophosphamide, ifosfamide, mechlorethamine, and melphalan).

IMPDH, including all of its isoform, may be a key rate-limiting enzyme for the purine biosynthesis pathway, as one of the ARL13B interacting partners during TMZ therapy. IMPDH is also known in the art as potentially being involved in oncogenesis.

IMPDH may control the gateway to purine nucleotides, by catalyzing the rate-limiting reaction of de novo GTP biosynthesis at the inosine monophosphate (IMP) metabolic branch point. This critical reaction appears to be present in every organism. Alternatively, purine bases, released by hydrolytic degradation of nucleic acids and nucleotides, can be salvaged and recycled. This may be an energy-saving pathway for purine biosynthesis, and its inefficiency may result in many pathological conditions including Lesch-Nyhan syndrome. In cancer, rapid cell division may result in a high demand for purine nucleotides that generally may not be able to be sustained by salvage pathways, which may explain the importance of IMPDH in cancer. Inhibitors of IMDPH are known in the art.

Suitable agents that inhibit the biological activity of IMDPH, or at least one of any of its isoforms, may include, but are not limited to the compound referred to as mycophenolic mofetil, which may be sold under the brand name CellCept, having the following formula or salt thereof:

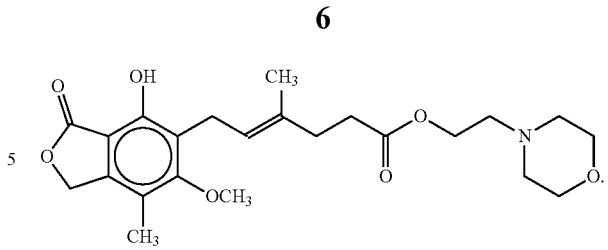

Suitable agents that inhibit the biological activity of IMDPH, or at least one of any of its isoforms, may include, but are not limited to the compound referred to as mizoribine having the following formula or salt thereof:

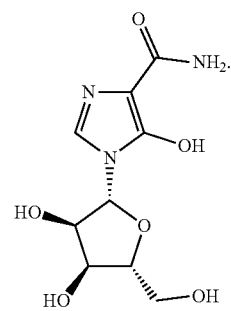 [SMILES: NC(=O)c1ncn([C@@H]2O[C@H](CO)[C@@H](O)[C@H]2O)c1O]

Suitable agents that inhibit the biological activity of IMDPH, or at least one of any of its isoforms, may include, but are not limited to the compound referred to as ribavirin having the following formula or salt thereof:

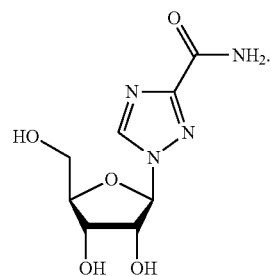

Suitable agents that inhibit the biological activity of IMDPH, or at least one of any of its isoforms, may include, but are not limited to the compound referred to as tiazofurin having the following formula or salt thereof:

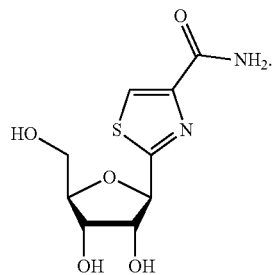

Suitable agents that inhibit the biological activity of IMDPH, or at least one of any of its isoforms, may include, but are not limited to the compound referred to as mycophenolic acid having the following formula or salt thereof:

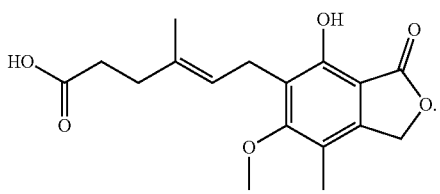 [SMILES: COc1c(C)c2c(c(O)c1C/C=C(\C)CCC(=O)O)C(=O)OC2]

In some embodiments, the disclosed methods and compositions relate to treating a proliferative cell disease or disorder in in a subject in need thereof by administering to the subject a combination of therapies selected from (i) administering a therapeutic agent that inhibits the biological activity of ARL13B to the subject; and/or (ii) administering an alkylating agent to the subject (e.g., temozolomide); and/or (iii) administering a therapeutic agent that inhibits the biological activity of IMPDH1, IMPDH2, another isoform of IMPDH, or any combination thereof to the subject. Suitable subject may include, but are not limited to subjects having brain cancer such as glioblastoma multiforme (GBM).

The combined treatment of administering radiation therapy and temozolomide for treating GBM is referred to as the "Stupp Protocol." In some embodiments, of the disclosed methods, a subject undergoing the Stupp Protocol is administered a therapeutic agent that inhibits the biological activity of ARL13B and/or IMPDH1, IMPDH2, another isoform of IMPDH, or any combination thereof, either before, concurrently with, or after the Stupp Protocol.

In the disclosed methods, the therapeutic agents may be administered by any suitable route of administration. In some embodiments, the therapeutic agents of the disclosed methods may be administered by any suitable route of delivery, including but not limited to, oral delivery and intravenous delivery. In the disclosed methods, the alkylating agents may be administered by any suitable route of administration. In some embodiments, the alkylating agents of the disclosed methods may be administered by any suitable route of delivery, including but not limited to, oral delivery and intravenous delivery.

In the disclosed methods, the alkylating agent may be dosed in any amount or varying amounts that may be necessary to be effective. In some of the disclosed methods where an included alkylating agent is temozolomide, the temozolomide may be administered in one or more daily doses of 5 mg/m$^2$, 20 mg/m$^2$, 100 mg/m$^2$, 140 mg/m$^2$, 180 mg/m$^2$, 250 mg/m$^2$, 300 mg/m$^2$, or 400 mg/m$^2$, or within any range bounded therein. In some of the disclosed methods where an included alkylating agent is temozolomide, the temozolomide may be administered in doses of up to 200 mg/m$^2$ daily. In some of the disclosed methods where an included alkylating agent is temozolomide, the temozolomide may be administered in doses ranging from to 100 mg/m$^2$ daily to 300 mg/m$^2$ daily. In some of the disclosed methods where an included alkylating agent is temozolomide, the temozolomide may be administered in doses up to 75 mg/m$^2$ daily. In some of the disclosed methods where an included alkylating agent is temozolomide, the temozolomide may be administered in doses ranging from 50 mg/m$^2$ daily to 100 mg/m$^2$.

In the disclosed methods, the alkylating agent may be administered for any length or lengths of time that may be necessary or effective. In the disclosed methods, there may be breaks between administrations of an alkylating agent for any length or lengths of time that may be necessary or effective. In some of the disclosed methods where an included alkylating agent is temozolomide, the temozolomide may be administered for a single cycle. In some of the disclosed methods where an included alkylating agent is temozolomide, the temozolomide may be administered for multiple cycles. In some of the disclosed methods where an included alkylating agent is temozolomide, the temozolomide may be administered for multiple cycles of substantially equivalent length. In some of the disclosed methods where an included alkylating agent is temozolomide, the temozolomide may be administered for an initial cycle with a length that differs from subsequent cycles. In some of the disclosed methods where an included alkylating agent is temozolomide, the temozolomide may be administered for an initial cycle with a length of up to 29 days. In some of the disclosed methods where an included alkylating agent is temozolomide, the temozolomide may be administered for an initial cycle with a length ranging from 20 to 35 days. In some of the disclosed methods where an included alkylating agent is temozolomide, the temozolomide may be administered for an initial cycle with a length ranging from 22 to 29 days. In some of the disclosed methods where an included alkylating agent is temozolomide, the temozolomide may be administered for an initial cycle with a length ranging from 49 days. In some of the disclosed methods where an included alkylating agent is temozolomide, the temozolomide may be administered for an initial cycle with a length ranging from 35 to 55 days. In some of the disclosed methods where an included alkylating agent is temozolomide, the temozolomide may be administered for an initial cycle with a length ranging from 42 to 49 days. In some of the disclosed methods where an included alkylating agent is temozolomide, following an initial cycle the temozolomide may be administered for an at least one subsequent cycle. In some of the disclosed methods where an included alkylating agent is temozolomide, following an initial cycle the temozolomide may be administered for an at least two subsequent cycles. In some of the disclosed methods where an included alkylating agent is temozolomide, following an initial cycle the temozolomide may be administered for an at least three subsequent cycles. In some of the disclosed methods where an included alkylating agent is temozolomide, following an initial cycle, temozolomide may be administered for at least one of the subsequent cycle that lasts at least 3 days. In some of the disclosed methods where an included alkylating agent is temozolomide, following an initial cycle, temozolomide may be administered for at least one of the subsequent cycle that lasts at least 5 days. In some of the disclosed methods where an included alkylating agent is temozolomide, following an initial cycle, temozolomide may be administered for at least one of the subsequent cycle that lasts at least 10 days.

In the disclosed methods, the therapeutic agent may be dosed in any amount or amounts that may be necessary to be effective. In the disclosed methods, where the therapeutic agent administered is mycophenolic mofetil, the mycophenolic mofetil may be administered in an amount of 1 mg, 1.5 mg, 2 mg, 2.5 mg, 3 mg, 3.5 mg, 4 mg, 5 mg, 10 mg, or within any range bounded therein. In the disclosed methods, where the therapeutic agent administered is mycophenolic mofetil, the mycophenolic mofetil may be administered in an amount of 2 mg daily. In the disclosed methods, where the therapeutic agent administered is mycophenolic mofetil, the mycophenolic mofetil may be administered in an amount of 3 mg daily. In the disclosed methods, where the therapeutic agent administered is mycophenolic mofetil, the dosage of mycophenolic mofetil may be administered 1-time-daily, 2-times-daily, 3-times-daily, 4-times-daily, or any combination thereof. In the disclosed methods, where the therapeutic agent administered is mycophenolic mofetil, the mycophenolic mofetil may be administered orally, intravenously, or any combination thereof.

In the disclosed methods, the therapeutic agent may be dosed in any amount or amounts that may be necessary to be effective. In the disclosed methods, where the therapeutic agent administered is mizoribine, the mizoribine may be administered in an amount of 0.25 mg/kg/day, 1 mg/kg/day, 1.5 mg/kg/day, 2 mg/kg/day, 2.5 mg/kg/day, 3 mg/kg/day, 3.5 mg/kg/day, 4 mg/kg/day, 5 mg/kg/day, 6 mg/kg/day, 10 mg/kg/day, 12 mg/kg/day, 15 mg/kg/day, 20 mg/kg/day, 25 mg/kg/day or within any range bounded therein. In the disclosed methods, where the therapeutic agent administered is mizoribine, the mizoribine may be administered in an amount of 3 mg daily. In the disclosed methods, where the therapeutic agent administered is mizoribine, the mizoribine may be administered in an amount of 6 mg daily. In the disclosed methods, where the therapeutic agent administered is mizoribine, the mizoribine may be administered in an amount of 9 mg daily. In the disclosed methods, where the therapeutic agent administered is mizoribine, the mizoribine may be administered in an amount of 12 mg daily. In the disclosed methods, where the therapeutic agent administered is mizoribine, the mizoribine may be administered 1-time-daily, 2-times-daily, 3-times-daily, 4-times-daily, or any combination thereof. In the disclosed methods, where the therapeutic agent administered is mizoribine, the izoribine may be administered 1-time-daily. In the disclosed methods, where the therapeutic agent administered is mizoribine, the mizoribine may be administered 2-times-daily. In the disclosed methods, where the therapeutic agent administered is mizoribine, the mizoribine may be administered orally, intravenously, or any combination thereof.

DESCRIPTION

Purines, the most abundant metabolic substrates, function as the building blocks for DNA and RNA. Since uncontrolled cell proliferation is the hallmark of cancer, purines are vital in this aberrant process. Cancer cells typically use the de novo biosynthesis pathway, whereas the central nerves system (CNS), as well as CNS malignancy including glioblastoma, usually rely more on the salvage pathway because of the high energy requirement for de novo pathway (PMID: 2154328). Through unbiased gene expression analysis, we have identified ARL13B as a novel regulator of the purine biosynthesis pathway by directly interacting with inosine monophosphate dehydrogenase 2 (IMPDH2), a key rate-limiting enzyme this pathway. The alkylating chemotherapy temozolomide (TMZ) is one of the few chemotherapeutic options against GBM due to its blood-brain barrier-permeable capacity. TMZ exerts its anti-tumor effect by generating a range of DNA lesions by predominately alkylating cellular purines. We have discovered that the ARL13B-IMPDH2 interaction promotes resistance against the alkylating chemotherapy by allowing the cancer cells to support their nucleotide demand via the de novo pathway, thus enabling them to avoid recycling of the alkylated nucleotides during chemotherapy and evade chemotherapy-induced DNA damage. The major technological advancement with this proposal is the repurposing of clinically proven (Mizoribine) and FDA approved (CellCept) compounds that modulate this ARL13B and IMPDH2 interaction and produce robust survival benefits in vivo and vitro models. These therapies are efficacious and can be rapidly translated into clinics due to their wide use and minimal side effects in order to rapidly improve standard of care for glioblastoma patients. Ultimately, we are proposing that by targeting this pathway by repurposing FDA approved and internationally studied drugs CellCept and Mizoribine, we can overcome the chemoresistance properties of GBM and improve the clinical efficacy of conventional therapies.

Using an antibody-mediated pulldown and subsequent mass spectrometric analysis we were able to characterize a novel binding partner interaction between ARL13B and IMPDH2. ARL13B is a protein canonically involved in the generation of cellular cilia and has been studied in connection to sonic hedgehog signaling and even implicated in a ciliary disorder called Joubert syndrome (PMID: 18674751) IMPDH2 is an enzyme that catalyzes the rate-limiting step of De-novo purine biosynthesis in cells and is thus critically important for cellular development. All cells in the body carry the need to utilize purines and pyrimidines in order to maintain cellular proliferation and continue to synthesize DNA. This holds true especially in cells that rapidly proliferate and divide such as cancer cells. Under normative conditions cells possess the ability to choose between two routes of purine and pyrimidine synthesis, De-Novo or Salvage synthesis. The de-novo synthesis starts with a ribose ring and through a series of reactions constructs purines for use in DNA and RNA from a starting substrate including amino acids and bicarbonate.

In comparison, salvage pathway synthesis is a less complex and energy-intensive reaction which creates purine or pyrimidine bases by catabolism of free nucleic acids or other cofactors. Because of our characterization of this novel interaction we were interested to learn whether ARL13B and IMPDH2 played a cooperating role in any of the purine biosynthesis pathways. To accomplish this, we utilized CRISPR to genetically knockout AR13B expression and subjected our cells to radiolabeled isotope tracing to assay the utilization of both the De-Novo and Salvage purine biosynthesis pathways. Upon examination 14C radioisotope labeled glycine tracing showed a significant reduction in De-Novo purine biosynthesis in the cells without ARL13B expression when compared to controls, and 3H radioisotope-labeled hypoxanthine tracing showed a 6-fold upregulation in salvage pathway utilization in the cells without ARl13B expression. This demonstrated to us that the ARl13B and IMPDH2 interaction was essential in allowing cells to utilize De-Novo purine biosynthesis as when it was removed Salvage pathway biosynthesis dominated.

Interestingly, the current standard of care therapy for Glioblastoma is an alkylating chemotherapeutic agent called Temozolomide which exerts its primary form of toxicity through DNA alkylation of purine bases specifically resulting in the creation of 60-Methylguanine. Creation of this alkylated purine causes a base pair mismatch in DNA (G-T) which results in DNA damage and cell cycle arrest and apoptosis (PMID: 15322239). Because of the nature of temozolomide chemotherapy-induced DNA damage, we chose to examine whether or not salvage pathway synthesis carried an implicit sensitivity to this alkylating chemotherapy. Again using radiolabeled isotope tracing, we were able to demonstrate that temozolomide therapy did not statistically change the purine biosynthetic flux through the De-Novo pathway. However, it did decrease the utilization of the salvage pathway by roughly 50%. Next, we subjected our ARL13B knockout cells to a standard dose of Temozolomide chemotherapy and checked whether they had more DNA double-stranded breaks by utilizing gamma h2ax foci counting. When compared to cells with endogenous ARL13B expression the knockdown cells demonstrated significantly more foci during therapy. This affirmed to us that the forced utilization of salvage pathway synthesis by these cells might be causing them to uptake more alkylated purines and thus incur more DNA damage than would normally occur from standard Temozolomide treatment. With this sensitivity in mind, we generated a viral knockout of AR13B expression in a series of patient-derived xenograft lines representing all molecular subtypes of the disease and injected them into the brains of nude mice. After exposure to a sub-optimal (2.5 mg/kg) dose of temozolomide chemotherapy (or vehicle control) for five days, we demonstrate that knockdown of ARL13B, and subsequent disruption of the ARL13B and IMPDH2 interaction greatly extends the survival of mice. Furthermore, cooperative effects with temozolomide treatment are seen further extending survival over knockdown of ARL13B alone. Overall, this data leads us to believe that we can augment the effectiveness of temozolomide chemotherapy by disrupting the novel ARL13B and IMPDH2 interaction and thus forcing the cells to undergo salvage synthesis and uptake purines damaged by temozolomide.

IMPDH is an extensively investigated molecular target for potential immunosuppressive, antiviral and anti-cancer chemotherapy (PMID: 21426047). Until now, two non-competitive and reversible inhibitors of IMPDH, CellCept (mycophenolate mofetil) and Mizoribine (approved in Asia), have been used clinically against autoimmunity (PMID: 27903231).

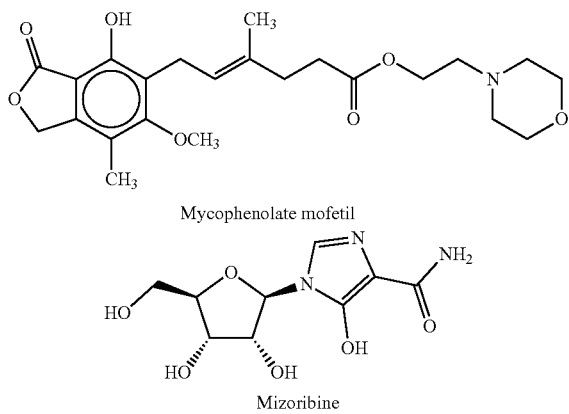

Mycophenolate mofetil

Mizoribine

Numerous studies have demonstrated the potential of this class of drugs as anti-cancer agents, and a number of phase I clinical trials with different cancers are ongoing (PMID: 22669334,15623606). Among these drugs, CellCept demonstrated the ability to cross the blood-brain barrier (BBB) and promoted neuroprotection against various inflammatory conditions including EAE and stroke (PMID: 24496150, 28011882). Based on our preliminary data, we now seek to investigate if blocking the IMPDH-mediated de novo pathway will sensitize GBM cells towards alkylating chemotherapy such as TMZ and Carmustine (BCNU) both in vitro and in vivo. We have identified a Food and Drug Administration (FDA) approved IMPDH inhibitor CellCept that can be repurposed for preventing GBM resistance against TMZ. In an animal and in vitro model CellCept significantly improved the therapeutic efficacy of TMZ-based anti-GBM chemotherapy, based on this, we are proposing that by targeting this pathway by repurposing FDA approved drug CellCept we can overcome the chemoresistance properties of GBM and improve the clinical efficacy of conventional therapies. Other compounds exist for targeting IMPDH, for example Mizoribine, which is widely used in other countries such as Japan as an immunosuppressant (PMID: 10390602, 11896886). This adds merit to our project in that there are a number of compounds that have been well studied and proven to be safe in humans which we can repurpose to significantly impact survival in glioma.

ILLUSTRATIVE EMBODIMENTS

The following Embodiments are illustrative and should not be interpreted to limit the scope of the claimed subject matter.

Embodiment 1. A method of treating a proliferative cell disease or disorder in a subject in need thereof, the method comprising: (a) administering to the subject a therapeutic agent that inhibits or reduces the biological activity of IMDPH1 or IMDPH2; and (b) administering to the subject an alkylating agent.

Embodiment 2. The method of embodiment 1, wherein the therapeutic agent that inhibits or reduces the biological activity of IMDPH1 or IMDPH2 is selected from the group consisting of mizoribine, ribavirin, tiazofurin, mycophenolic mofetil, mycophenolic acid, and a derivative of mycophenolic acid.

Embodiment 3. The method of embodiment 1 or 2, wherein the therapeutic that inhibits or reduces the biological activity of IMDPH1 or IMDPH2 is selected from mizoribine, mycophenolic mofetil, or mycophenolic acid.

Embodiment 4. The method of any of the foregoing embodiments, wherein the alkylating agent is selected from the group consisting of triazenes, nitrogen mustards, nitrosoureas, alkyl sulfates, and ethyleninimines.

Embodiment 5. The method of any of the foregoing embodiments, wherein the alkylating agent is 3,4-dihydro-3methyl-4-oxoimidazo[5,1-d]-1,2,3,5-tetrazine-8-carboxamide otherwise known as temozolomide.

Embodiment 6. The method of any of the foregoing embodiments, wherein the proliferative cell disease or disorder is cancer.

Embodiment 7. The method of any of the foregoing embodiments, wherein the proliferative cell disease or disorder is a brain cancer.

Embodiment 8. The method of any of the foregoing embodiments, wherein the proliferative cell disease or disorder is a glioblastoma.

Embodiment 9. The method of any of the foregoing embodiments, wherein the proliferative cell disease or disorder is an astrocytoma.

Embodiment 10. The method of any of the foregoing embodiments, wherein the therapeutic agent is administered to the subject prior to the alkylating agent.

Embodiment 11. The method of any of the foregoing embodiments, wherein the therapeutic agent is administered orally.

Embodiment 12. The method of any of the foregoing embodiments, wherein the alkylating agent is administered orally.

Embodiment 13. A method of treating a proliferative cell disease or disorder in a subject in need thereof, the method comprising: (a) administering to the subject a therapeutic agent that down-regulates expression of ALRL13B or that inhibits biological activity of ARL13B; and (b) administering to the subject an alkylating agent.

Embodiment 14. The method of embodiment 13, wherein the alkylating agent is selected from the group consisting of triazenes, nitrogen mustards, nitrosoureas, alkyl sulfates, and ethyleninimines.

Embodiment 15. The method of embodiment 13 or 14, wherein the alkylating agent is 3,4-dihydro-3methyl-4-oxo-imidazo[5,1-d]-1,2,3,5-tetrazine-8-carboxamide, otherwise known as temozolomide.

Embodiment 16. The method of any of embodiments 13-15, wherein the proliferative cell disease or disorder is cancer.

Embodiment 17. The method of any of embodiments 13-15, wherein the proliferative cell disease or disorder is a brain cancer.

Embodiment 18. The method of any of embodiments 13-15, wherein the proliferative cell disease or disorder is a glioblastoma.

Embodiment 19. The method of any of embodiments 13-15, wherein the proliferative cell disease or disorder is an astrocytoma.

Embodiment 20. The method of any of embodiments 13-19, wherein the therapeutic agent is administered to the subject prior to the alkylating agent.

Embodiment 21. The method of any of embodiments 13-20, wherein the therapeutic agent is administered orally.

Embodiment 22. The method of any of embodiments 13-21, wherein the alkylating agent is administered orally.

Embodiment 23. The method of any of embodiments 13-22, wherein the therapeutic agent inhibits ARL13B from interacting with IMDPH1 or IMDPH2.

Embodiment 24. A kit for the treatment of a proliferative cell disease or disorder in a subject in need thereof, comprising as components: (a) a therapeutic agent that that inhibits or reduces biological activity of IMDPH1 or IMDPH2; and (b) an alkylating agent.

Embodiment 25. The kit of embodiment 24, wherein the therapeutic that inhibits or reduces the biological activity of IMDPH1 or IMDPH2 is selected from the group consisting of mizoribine, ribavirin, tiazofurin, mycophenolic mofetil, mycophenolic acid, and a derivative of mycophenolic acid mycophenolic acid.

Embodiment 26. The kit of embodiment 24 or 25, wherein the therapeutic that inhibits or reduces the biological activity of IMDPH or IMDPH2 is selected from mizoribine, mycophenolic mofetil, or mycophenolic acid.

Embodiment 27. The kit of any of embodiments 24-26, wherein the alkylating agent is selected from the group consisting of triazenes, nitrogen mustards, nitrosoureas, alkyl sulfates, and ethyleninimines.

Embodiment 28. The kit of any of embodiments 24-26, wherein the alkylating agent is 3,4-dihydro-3methyl-4-oxo-imidazo[5,1-d]-1,2,3,5-tetrazine-8-carboxamide otherwise known as temozolomide.

Embodiment 29. The kit of any of embodiments 24-28, wherein the therapeutic agent of component (a) is formulated for oral administration.

Embodiment 30. The kit of any of embodiments 24-29, wherein the therapeutic agent of component (b) is formulated for oral administration.

EXAMPLES

The following Examples are illustrative and should not be interpreted to limit the scope of the claimed subject matter.

Example 1—ARL13B Interacts with IMPDH2 to Modulate Purine Synthesis and Temozolomide Resistance in Glioblastoma Reference is made to the Annual Meeting-Society of Neuro-Oncology 2018 (Nov. 15-18, 2018; New Orleans, La.)

Glioblastoma, a universally lethal primary brain tumor, harnesses cellular plasticity to drive therapeutic adaptation. Critical factors in developing this plasticity are histone modifiers such as Polycomb Repressor Complex 2 protein EZH2. In order to examine tumor cell plasticity in depth, we conducted multiple ChIP Sequencing runs and demonstrate that EZH2 binds within an enhancer region of ARL13B during temozolomide (TMZ) therapy and induces an H3K4 mono-methylation mark. Concurrently, we observed an increase in H3K27ac at the transcription start site of ARL13B as well as a lack of H3K27 tri-methylation, EZH2's canonical histone mark. Based on this we hypothesize that EZH2 could be non-canonically regulating ARL13B to allow for cellular plasticity and ultimately drive therapeutic adaptation. Delving further into this regulation we demonstrate that knockdown of ARL13B in patient derived xenograft cells significantly increased survival of mice in an orthotopic GBM model when compared to controls (p-value<0.0001). The Cancer Genome Atlas (TCGA) patient dataset demonstrates time to recurrence in patients with downregulated ARL13B is substantially increased as compared to ARL13B upregulated patients (log-rank p-value=0.0012). Searching for a mechanism behind this survival benefit, we preformed mass spectrometry on an ARL13B pulldown in a patient derived xenograft line during TMZ therapy and identified inosine monophosphate dehydrogenase 2 (IMPDH2), the rate-limiting enzyme in de-novo guanine nucleotide biosynthesis, as a significant binding partner of ARL13B during TMZ chemotherapy (p-value<0.0001). Probing this novel interaction further we examined the de-novo and salvage purine biosynthesis pathways using radiolabeled carbon tracing experiments. In ARL13B knockdown cells, purine salvage pathway usage is upregulated 7-fold (p-value<0.0001) while de-novo pathway usage was decreased about 50% (p-value=0.004) in a TMZ specific manner. Examination of IMPDH2 enzymatic activity using a formazin reduction assay demonstrated a decrease in activity over 8 days of TMZ exposure (p<0.001). Moreover, ARL13B knockdown GBM cells treated with TMZ show a robust increase in DNA double-strand breaks compared to control cells exposed to TMZ, demonstrated by γH2X staining. Finally, a potent inhibitor of IMPDH2 (Mycophenolate Mofetil) significantly extended median survival in an orthotopic PDX mouse model only when in combination with TMZ (p<0.01). Based on these data we hypothesize that EZH2 regulates a novel ARL13B and IMPDH2 interaction which when lost forces cells into salvage synthesis exclusively. This synthesis shift forces cells to uptake and incorporate purines that have been alkylated by TMZ therapy which increases DNA double strand breaks and ultimately impairs therapeutic adaptation.

Example 2—Ciliary Protein ARL13B Promotes Chemoresistance by Modulation of Glioblastoma Purine Biosynthesis Reference is made to the American Association of Cancer Research Annual Meeting 2019 (Mar. 29-Apr. 3, 2019; Atlanta, Ga.).

Glioblastoma (GBM) carries with it an almost 100% recurrence rate due to development of resistance to all conventional therapies. Our lab has demonstrated ARL13B, an ADP-ribosylation factor-like protein critical for cilia formation, plays an important role in promoting resistance to temozolomide (TMZ)-based chemotherapy. Knockdown of ARL13B in patient derived xenograft cells significantly increased survival of mice in an orthotropic GBM model when compared to controls (p-value<0.0001). The Cancer Genome Atlas (TCGA) patient dataset demonstrates time to recurrence in patients with downregulated ARL13B is substantially increased as compared to ARL13B upregulated patients (log-rank p-value=0.0012). To better understand the role of ARL13B in therapeutic adaptation we performed mass spectrometry analysis of an ARL13B pulldown during TMZ therapy and identified inosine monophosphate dehydrogenase 2 (IMPDH2), the rate-limiting enzyme in de-novo guanine nucleotide biosynthesis, as a significant binding partner of ARL13B during TMZ chemotherapy (p-value<0.0001). Immunoprecipitation analysis across multiple GBM cell lines validated this interaction and its increase during TMZ therapy. Probing this interaction further we examined the de novo and salvage purine biosynthesis pathways using radiolabeled carbon tracing experiments. In ARL13B knockdown cells, purine salvage pathway usage is upregulated 7-fold (p-value<0.0001) while de-novo pathway usage was decreased about 50% (p-value=0.004) in a TMZ specific manner. Moreover, ARL13B knockdown GBM cells treated with TMZ show a robust increase in DNA double-strand breaks compared to control cells exposed to TMZ, demonstrated by γH2X staining. Based on these observations, we hypothesize that ARL13B is a novel regulator of IMPDH2 allowing GBM cells to block salvage pathway biosynthesis to avoid TMZ induced DNA damage. However, when ARL13B is lost, GBM cells are forced into salvage pathway synthesis thus becoming sensitized to TMZ therapy due to increased incorporation of alkylated purines, a known function of TMZ.

Example 3—ARL13B Research Plan

Specific Aims

Glioblastoma (GBM) is an aggressive form of brain cancer with a dismal median survival of 20 months[1]. The implementation of blood-brain barrier-permeable alkylating chemotherapies, such as temozolomide (TMZ), combined with radiotherapy after surgery has improved overall survival time by about 4-6 months[2,3]. Nevertheless, almost all patients eventually fall into relapse since GBM cells can develop aggressive resistance to conventional therapy[4]. It is therefore critical to find an actionable target against therapeutic resistance in GBM in order to establish a more effective therapy for this deadly disease.

Purines, the most abundant metabolic substrates, function as the building blocks for DNA and RNA. Since uncontrolled cell proliferation is the hallmark of cancer, purines are vital in this aberrant process. Moreover, in some tumors, alteration in the purine biosynthesis pathway resulted in inherent resistance to chemotherapeutics[5,6]. In mammalian cells, purine nucleotides are synthesized through the de novo biosynthesis pathway and/or recycled via the salvage pathway[7-10]. In most proliferative cells including cancer cells, the de novo pathway is preferred. In GBM, however, the activity of the salvage pathway was reported to be higher than the de novo pathway[11]. Conversely, the therapy resistant glioma stem cells (GSCs) shows preferential use of the de novo biosynthesis pathway[12]. We have identified ciliary protein ARL13B as a novel regulator of the purine biosynthesis pathway during chemotherapy. Our immunoprecipitation-mass spectroscopy analysis revealed that ARL13B directly interacts with inosine monophosphate dehydrogenase 2 (IMPDH2), a key rate-limiting enzyme for purine biosynthesis. Isotope tracing under normal physiological conditions demonstrated that during TMZ treatment, salvage pathway activity was decreased by 50% while de novo pathway activity remains unchanged in the patient derived xenograft (PDX) models of GBM. In contrast, when ARL13B is knocked-out, the de novo pathway is inhibited in a TMZ-specific manner and salvage pathway utilization increases about 6-fold. Importantly, this switch to the salvage pathway in the ARL13B-knockout GBM cells elevated the number of cytotoxic DNA lesions and enhanced the effectiveness of the alkylating agent TMZ both in vitro and in vivo. Based on these data, we hypothesize that ARL13B-IMPDH2 regulated switch from the salvage pathway to the de novo purine biosynthesis pathway is necessary for GBM cells' adaptation to alkylating-based chemotherapy.

Our observation of this switch in purine biosynthesis during anti-GBM chemotherapy raises a number of fundamental questions, most importantly whether such a switch is controlled or incidental, and whether it is evolutionarily advantageous, deleterious, or neutral. We believe that activating the de novo purine biosynthesis pathway during therapy allows GBM cells to avoid recycling modified nucleotides resulting from the alkylation via chemotherapeutic TMZ. This in turn protects the cells from DNA damage while also maintaining a steady flow of purine building blocks to support uncontrolled proliferation. To investigate this, we propose the following aims:

Specific Aim 1: To investigate the role of ARL13B in regulating purine metabolism, we will first map out the ARL13B domain that interacts with IMPDH, characterize the interaction by surface plasmon resonance. We will then investigate the interaction dynamics between ARL13B and the two isoforms of IMPDH and examine the consequence of this interaction with regards to IMPDH enzymatic activity and kinetics. Finally, we will interrogate 30 matched primary and recurrent GBM patient samples to assess the clinical significance of this interaction.

Specific Aim 2: To elucidate the role of purine metabolism in promoting resistance to TMZ. To test this, we will first examine the purine biosynthesis pathway in vivo in the patient-derived xenograft (PDX) model using stable isotope tracing analysis. We will utilize a CRISPR knockout system to create GBM lines deficient in either the de novo or the salvage pathway and investigate its effect on i) DNA damage response during TMZ therapy, ii) therapy resistant cancer stem cell (CSC) biology iii) tumor engraftment and iv) therapeutic responses in vivo.

Specific Aim 3: To evaluate if regulation of purine biosynthesis is an actionable target in GBM to prevent resistance to alkylating-based chemotherapy. Based on our preliminary observation, we are proposing that targeting the de novo pathway could prevent resistance to alkylating chemotherapy. To inhibit the de novo pathway, we will employ a mycophenolate acid derivative, mycophenolate mofetil (MMF), an FDA approved blood-brain permeable drug and/or AVN944 that can selectively inhibit IMPDH activity and block de novo pathway[13,14]. MMF will be combined with TMZ therapy in the orthotopic PDX GBM to examine if regulating purine biosynthesis could enhance the efficacy of TMZ-based anti-glioma chemotherapy.

Collectively, these studies will provide novel insight into the role of the purine biosynthesis pathways in the context of therapeutic resistance and allow us to formulate novel strategies to prevent GBM recurrence. Such findings have direct translational value for a lethal disease that is very much in need of effective therapies.

Introduction

Glioblastoma (GBM): The World Health Organization grade IV GBM is the most prevalent and primary malignancy in the brain[15]. The recently completed Tumor Treating Field clinical trial reported that median survival of patient with GBM is 20 months, but this outcome reflects a population of patients selected for clinical trials with favorable clinical status[16]. In reality, the universal median survival is about 8-10 months despite the aggressive therapeutic intervention of maximal surgical resection followed by radio- and chemotherapy[2]. In recent years, GBMs have been extensively characterized at the molecular level without any real impact on the clinical outcome. This unfavorable prognosis is mainly due to the high rate of recurrence, as recurrent GBMs are often highly invasive and therapy-resistant. It is therefore imperative to understand the mechanisms contributing to the evolutionary path to fitness, which promote therapeutic resistance and disease recurrence.

Alkylating Chemotherapy: The implementation of blood-brain barrier-permeable alkylating chemotherapies, such as temozolomide (TMZ), combined with radiotherapy after surgery in the standard care protocol have improved the overall survival time by about 4-6 months. TMZ exerts its anti-tumor effect by generating a range of DNA lesions including an O6-methylguanine (O6mG) lesion. However, 5-year survival rates for GBM still remain less than 10% due to recurrence with chemoresistant tumors[3, 17]. Most conventional mechanisms of resistance are considered to be caused by either a higher expression of the enzyme O6-methylguanine-DNA methyltransferase (MGMT) that can repair the O6mG lesions and patients with methylated MGMT promoter and inferior expression of MGMT tend to respond favorably with TMZ therapy[4, 17, 18]. Nevertheless, almost all patients eventually fall into relapse irrespective of the MGMT or MMR status, thus signifying the need for actionable insights of chemoresistance in order to develop a more effective therapy for GBM.

Purine Biosynthesis: Purines, the most abundant metabolic substrates for all living organisms, function as the building blocks for DNA and RNA. Since uncontrolled cell proliferation is the hallmark of cancer, purines are always in high demand in this aberrant process. Purines and their derivatives widely participate in the biological process of oncogenesis, including host-tumor interaction and immune response[19]. Tumor cells are inherently more resistance to cytotoxic effects of the chemotherapeutic antimetabolites because of the progression-linked changes in their purine biosynthesis pathway[5, 6]. In mammalian cells, purines nucleotides are synthesized through the de novo biosynthesis pathway and/or recycled via the salvage pathway[7-10]. Generally, the salvage pathway accounts for most of the cellular demands of purines by recycling the degraded bases with specific enzymes. However, both pathways have been reported to be involved in the oncogenic process. In GBM, the activity of salvage enzymes was found to be 48-fold higher than that of the rate-limiting enzymes of the de novo pathway[11]. Contrary, the therapy-resistant cancer stem cell population in GBM preferentially utilize de novo pathway[12]. Even though these reports point towards the idea that purine biosynthesis may be critical for gliomagenesis, its precious role in promoting chemoresistance and GBM recurrence is yet to be elucidated.

Figure 1B:
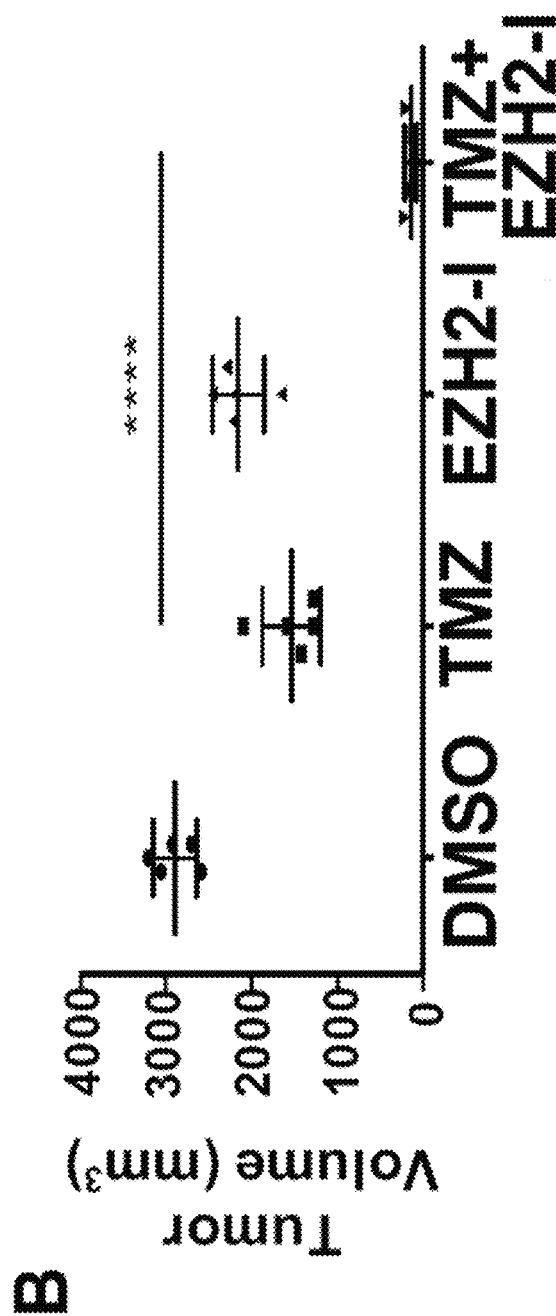

Preliminary Results:

2.1. Non-canonical function of EZH2 is necessary for therapeutic resistance against TMZ: Recent studies demonstrated that the epigenetic regulators partly govern therapeutic adaptation in cancer which induce transcriptome changes leading to therapeutic resistance[20, 21]. One such epigenetic regulator is the Polycomb Repressor Complex 2 (PRC2), a critical family protein that is essential for maintaining the self-renewal ability of adult and embryonic stem cells[22, 23]. This complex is involved in transcription silencing via chromatin compaction by catalyzing the methylation of the histone H3 at lysine 27. The catalytic subunit of the PRC2 complex, Enhancer Of Zeste 2 (EZH2), has been linked to aggressive progression of multiple cancers, including GBMs[24, 25]. The function of EZH2 is closely related to the cancer stem cell (CSC) phenotype, mesenchymal transition and radioresistance, which is associated with post-surgery relapse of GBM[24-26]. However, its role in promoting chemoresistance properties in GBM is yet to be investigated. To this end, we have examined the role of the EZH2-PRC2 complex in promoting TMZ resistance. We observed that post TMZ therapy, EZH2-positive GBM cells and CSC marker CD133-positive cells expressing EZH2 were significantly elevated in the in vivo orthotopic patient-derived xenograft (PDX) model as compared to untreated control (FIG. 1A). Blocking the EZH2 activity with a selective chemical inhibitor not only reduced the therapy-resistant CSC frequency (data not shown) but also significantly enhanced the therapeutic efficacy of TMZ in a GBM flank model (FIG. 1B). However, we were not able to achieve the similar results in the orthotopic PDX model since the EZH2 inhibitor failed to cross the blood-brain barrier.

In an effort to identify the downstream genes of EZH2-PRC2 complex, we next mapped out the EZH2 binding and histone 3 lysine 27 trimethylation (H3K27me3) enrichment on a genome-wide scale before and after exposure to temozolomide (TMZ) by preforming chromatin immunoprecipitation sequencing (ChIP-Seq) in two different subtypes of patient-derived xenograft model of GBM. For the temozolomide (TMZ) dose, we used 50 µM, since these are the reported peak cerebral spinal fluid and serum concentrations in patients[27-29]. We have identified 880 novel EZH2 binding sites and 130 new H3K27me3 sites specific to TMZ therapy (data not shown). Surprisingly, none of the post-therapy EZH2 enriched sites overlapped with the H3K27me3 enrichment (data not shown). When we investigated the global H3K27me3 during TMZ therapy, we observed a minimal change in immunoblot analysis (data not shown). Based on this data we concluded that EZH2-mediated TMZ resistance might not rely solely on methyltransferase activity.

Figures 1C, 1D:
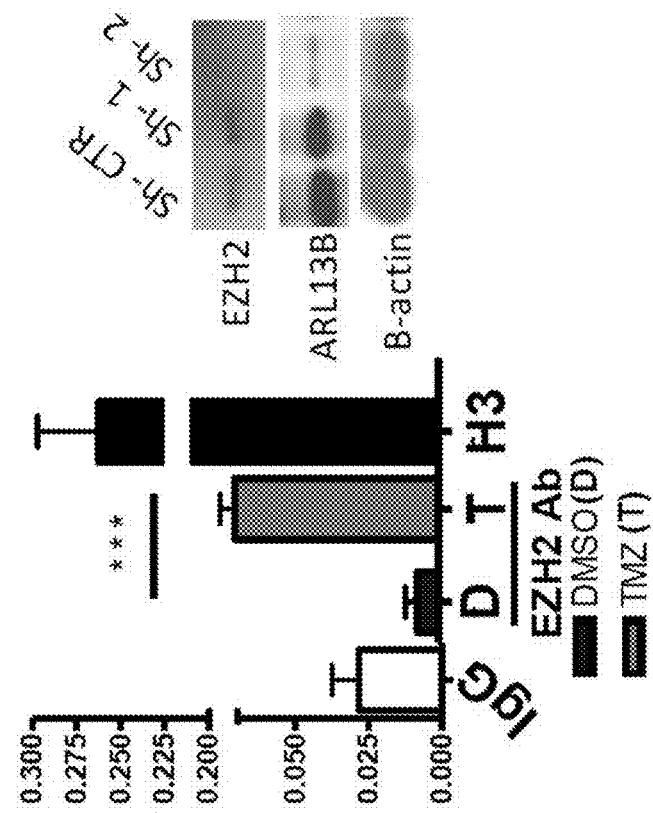

2.2. ARL13B is a downstream target of EZH2 non-canonical activity: Recent reports have demonstrated that oncogenic activity of EZH2 acts independently of PRC2. In prostate cancer, EZH2 can function as a transcriptional co-activator inducing the expression of androgen receptor downstream target genes[30]. Similarly, EZH2 interacts with RelA/RelB complex co-regulating subset of NF-kB targets increasing the aggressiveness of the breast cancer cells[31]. Based on these results, we investigated if the non-canonical function of EZH2 may be involved in chemoresistance in GBM. Sequence Microarray analysis was performed in two different subtypes of PDX lines treated with TMZ or TMZ+ EZH2 inhibitor to investigate if the non-canonical transcriptional activity was responsible for promoting TMZ resistance. ARL13B, a member of the ADP-ribosylation factor-like family protein accountable for cilia maintenance, was the top gene whose expression was significantly downregulated in the presence of EZH2 inhibitors (6-fold, p<0.05, FDR=0.05; FIG. 1C)[32]. ChIP-Seq analysis revealed that the binding of EZH2 in an ARL13B enhancer site was significantly enhanced during TMZ therapy (p<0.0001, FDR=0.0025) and ChIP qPCR analysis further validated (p<0.005). Finally, shRNA-mediated knockdown of EZH2 significantly downregulated the expression of ARL13B in GBM (data not shown).

Figures 2A, 2B:
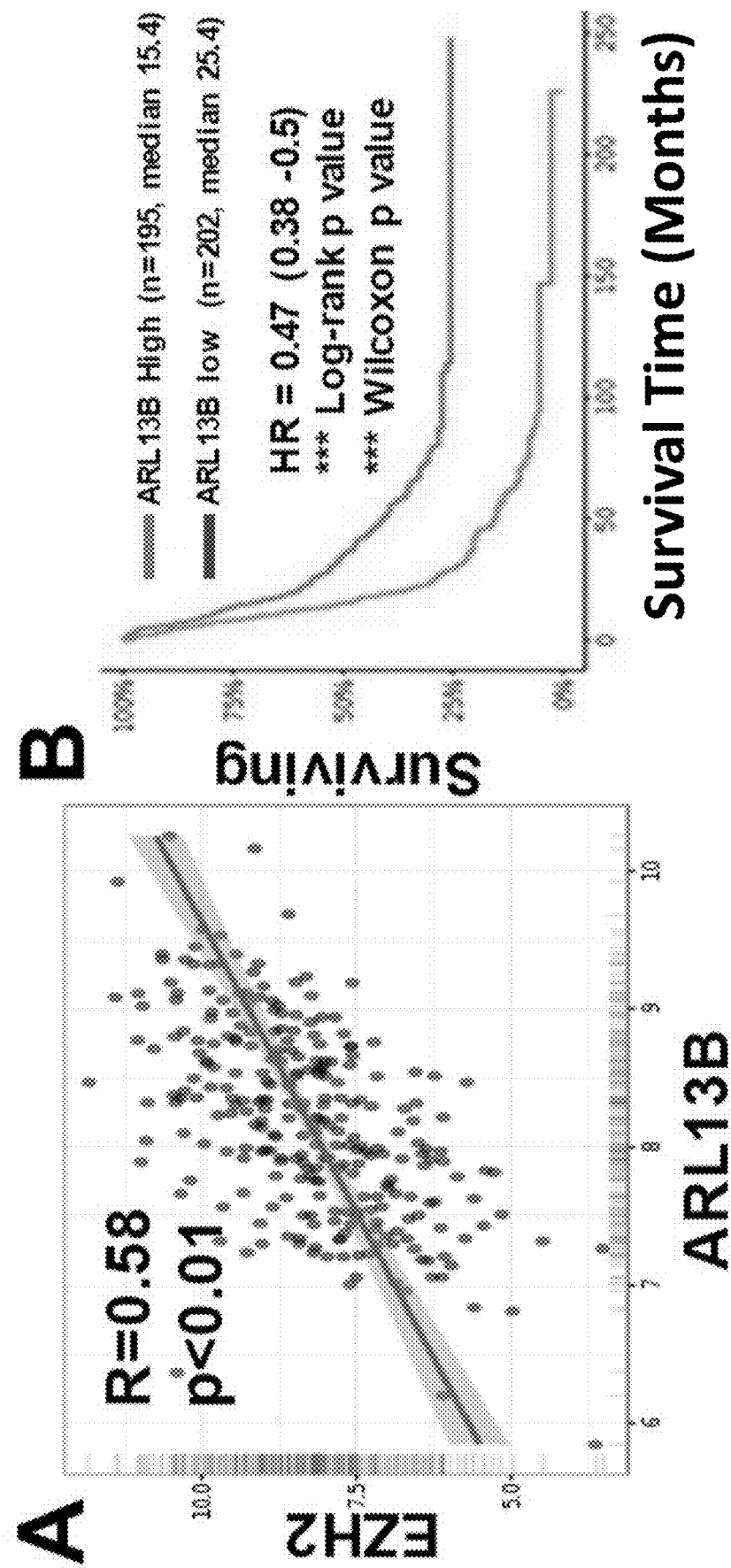
FIG. 2A-2F. Role of ARL13B in gliomagenesis. A) In TCGA data EZH2 directly correlates with ARL13B expression. B) ARL13B expression is positively correlated with GBM patient survival and time to recurrence (data not shown). C) Immunofluorescent analysis of ARL13B expression in PDX model showing localization in the cilia like structure. D) TMZ treatment increased the cilia size. E) and F) shRNA mediated knockdown of the ARL13B significantly blocks the in vivo tumor engraftment ability of two different subtypes of PDX (E) Proneural Subtype, (F) Classical subtype.
Figures 2C, 2D:
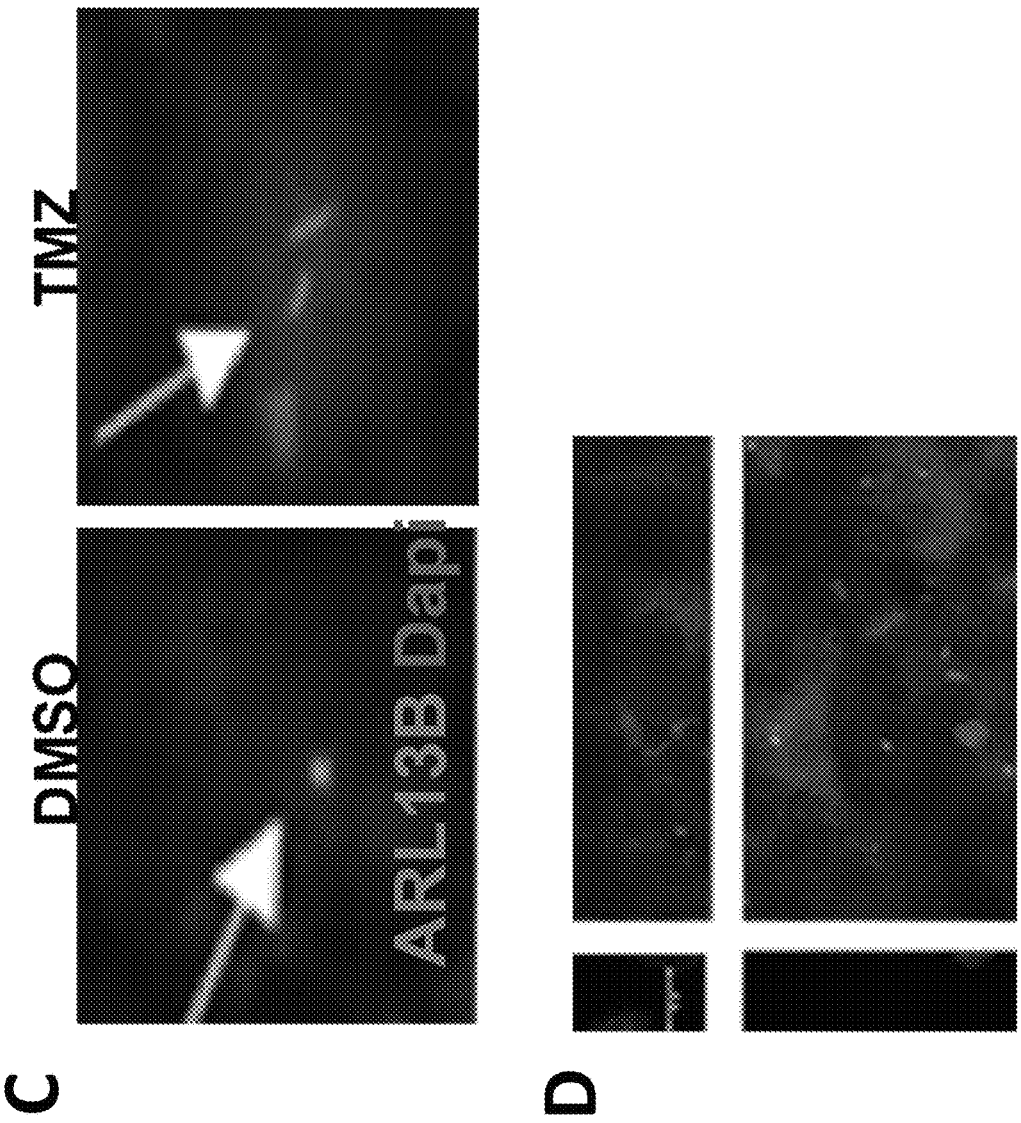

2.3. Role of ARL13B in gliomagenesis: ARL13B is a small GTPase that contains both N- and C-terminal guanine nucleotide-binding motifs. This protein is localized in cilia and plays a role in their formation. Mutations in this gene are the cause of Joubert syndrome. Disruption of ARL13B inhibits cilia-dependent oncogenic sonic hedgehog signaling (SHH) in medulloblastoma[33]. A recent report has demonstrated that GBM cells express cilia-like structures which were positive for ARL13B[34]. However, the role of ARL13b in gliomagenesis remains unknown. To investigate the clinical significance of ARL13B in GBM, we first interrogated the TCGA database and observed that not only is ARL13B overexpressed in GBMs (data not shown), but its expression is directly correlated with EZH2 expression (FIG. 2A). Most importantly, the ARL13B expression is negatively correlated with post-therapy GBM recurrence (FIG. 2B & data not shown). In the PDX model, ARL13B is located in cytoplasm as well as in the cilia (FIG. 2C) and TMZ therapy significantly increased the length of the Cilia (FIG. 2C). To examine ARL13B's role in vivo mice were orthotopically implanted with both classical and proneural subtype cells with confirmed shRNA mediated knockdown of ARL13b. While both subtypes showed distinct survival benefits the proneural subtype was especially sensitive to ARL13B knockdown with the mice receiving knockdown cells failing to have tumor engraftment. These preliminary results demonstrate that ARL13B presence plays a role in gliomagenesis and growth.

Figure 3A:
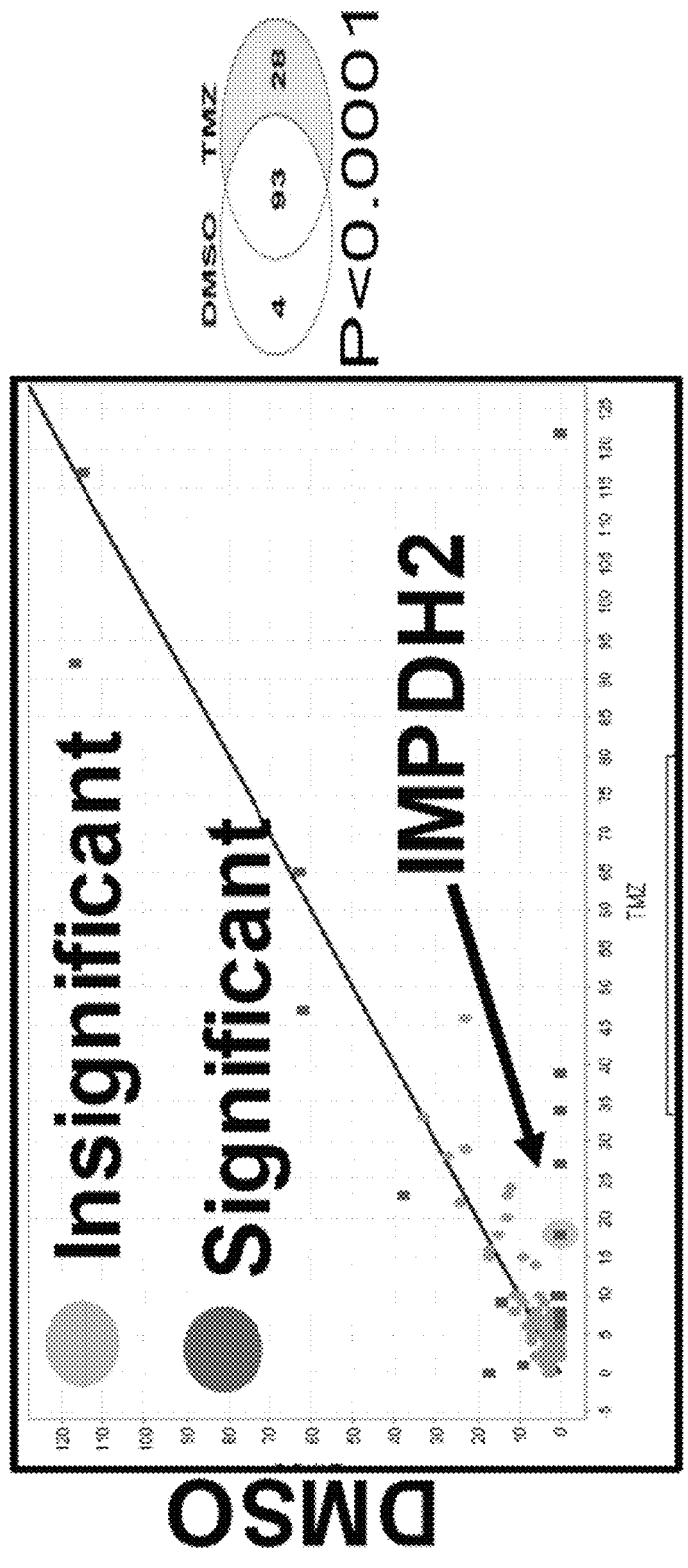
FIG. 3A-3B. ARL13B interacts with IMPDH2 during TMZ therapy. A) Mass spectroscopy (MS) analysis IMPDH2 as a novel interaction partner for ARL13B during TMZ therapy. Right, Venn diagram showing 28 new interactions with ARL13B during TMZ therapy. Yellow highlight showing 10 different peptides identified in MS analysis. B) Bidirectional IP-immunoblot analysis validating the MS results.
Figure 3B:
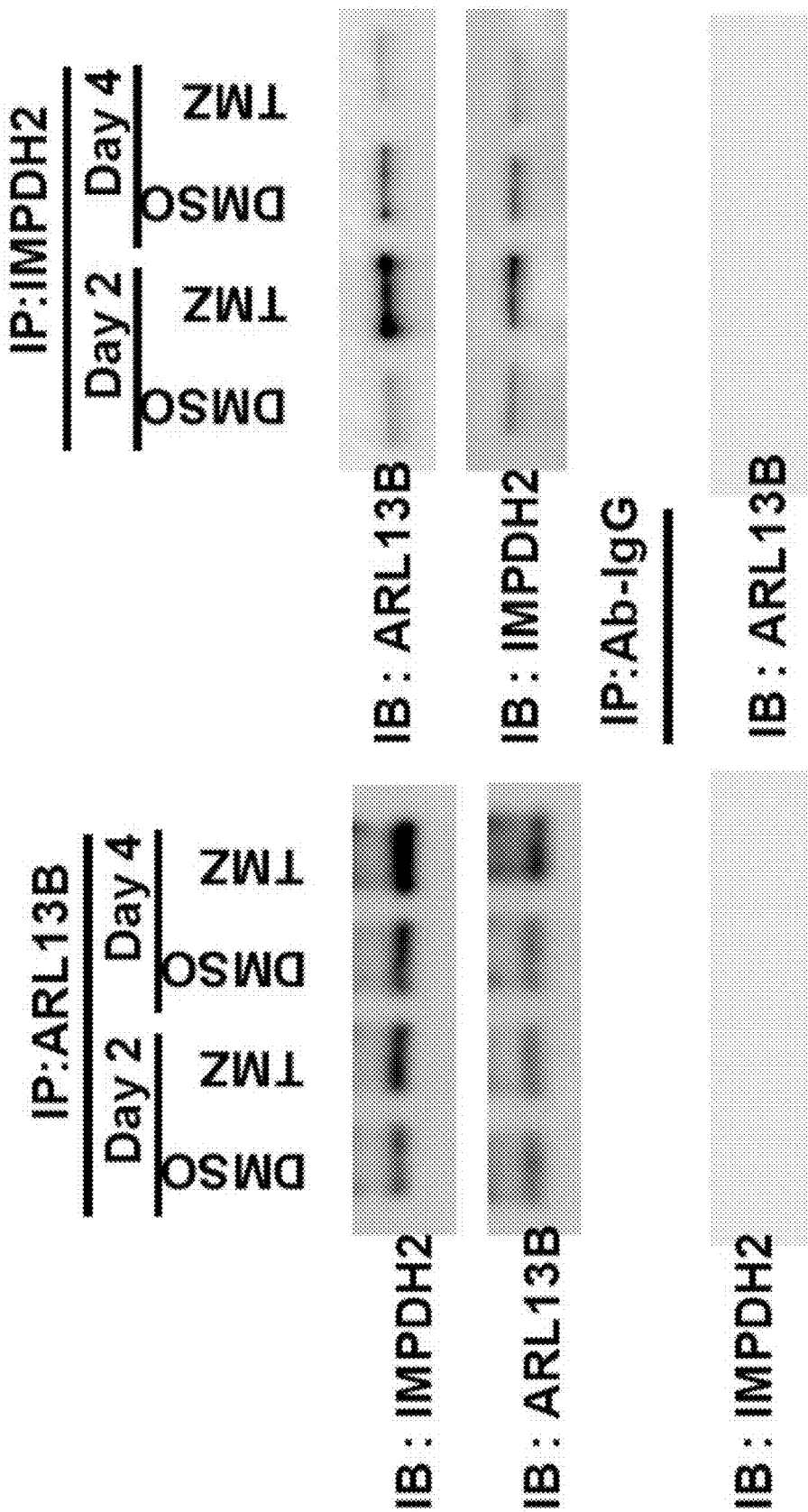

2.4. Identification of IMPDH2 as an ARL13B-interacting partner: We initially hypothesized that ARL13B might be involved in regulating cilia genesis, thus contributing to oncogenic SHH signaling in GBM during TMZ therapy[33-35]. However, our preliminary data indicated that SHH signaling was not altered during or post TMZ therapy (data not shown). To explore the mechanism by which ARL13B contributes to gliomagenesis and TMZ resistance, we captured candidate ARL13B-interacting partners during TMZ therapy by immunoprecipitation (IP) and subsequently identified them by mass spectroscopy (MS) in control- and TMZ-treated samples (FIG. 3A). We have identified 28 novel proteins that directly interact with ARL13B only during TMZ therapy. Many of these protein partners belong to the myosin gene family. Our screen also identified inosine-5' monophosphate dehydrogenase 2 (IMPDH2), a key rate-limiting enzyme for the purine biosynthesis pathway, as one of the ARL13B interacting partners during TMZ therapy. The MS identified ten unique peptides that covered about 23% of IMPDH2 amino acid sequence (FIG. 3A, right, highlighted in yellow). This interaction was further validated by IP-immunoblot analysis using an antibody against ARL13B and IMPDH2 (FIG. 3B) in multiple cell lines (data not shown). Based on this, we propose that ARL13B is a novel interacting partner for IMPDH2 during TMZ therapy.

Figures 2E, 2F:
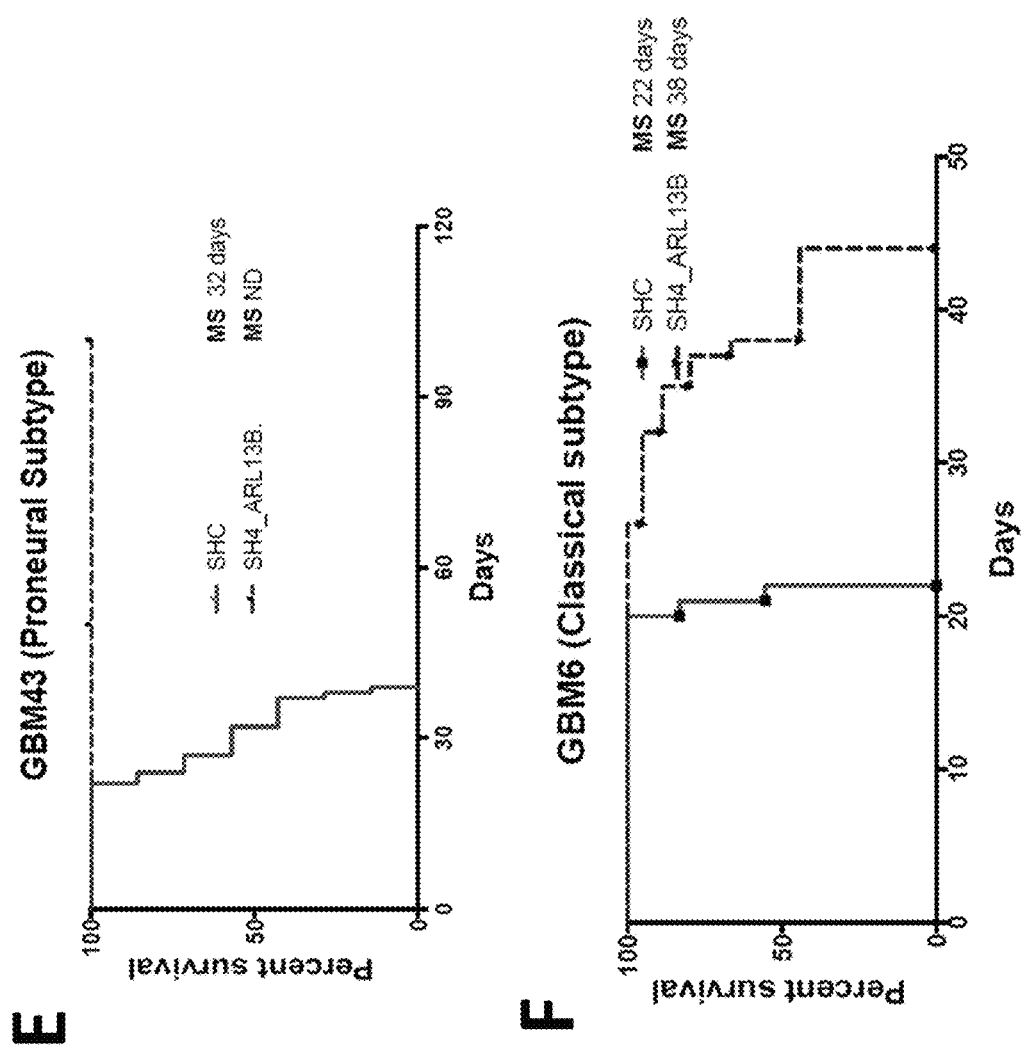
Figure 4A:
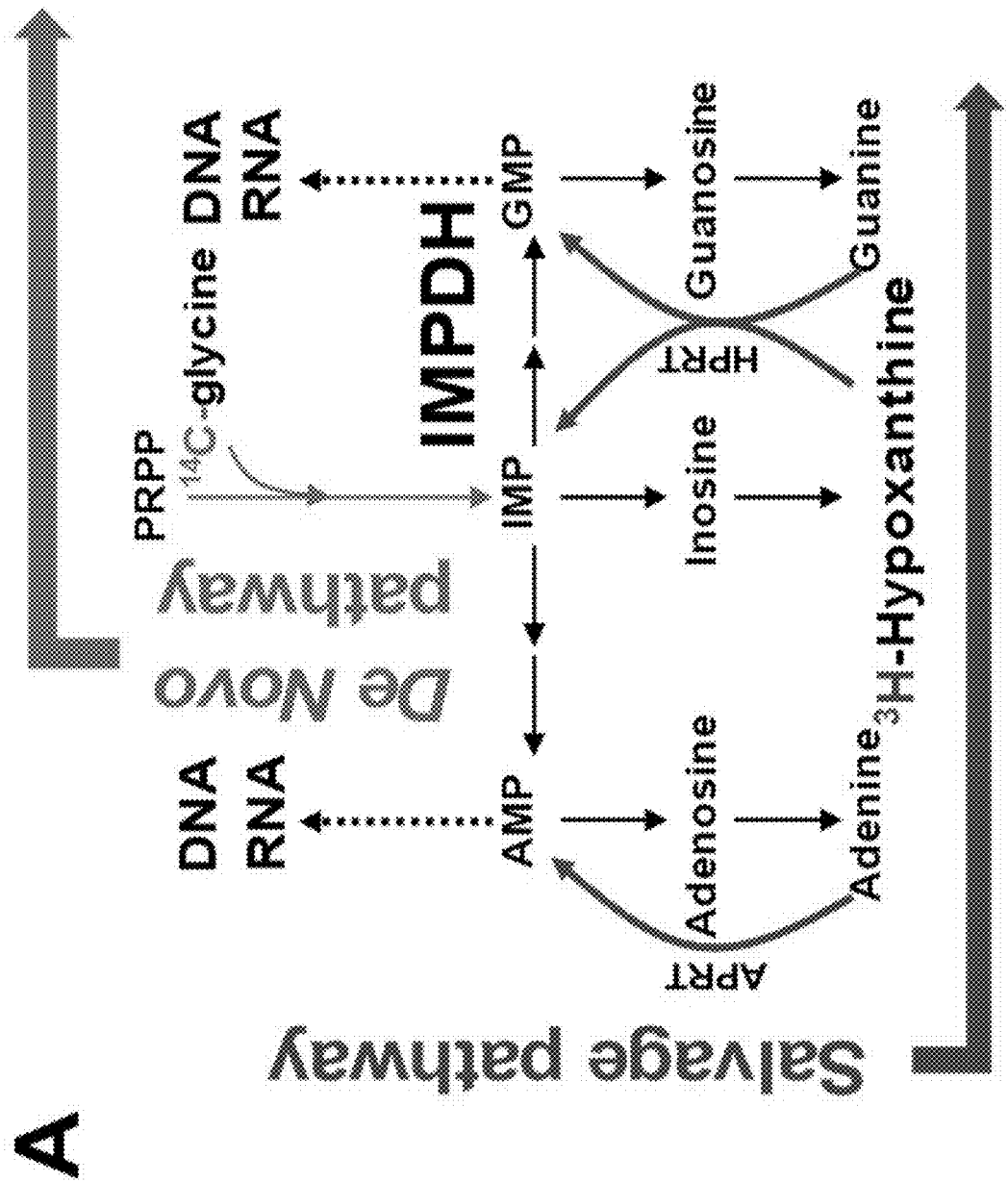
FIG. 4A-4E. IMPDH2-ARL13B interaction during TMZ therapy influences purine biosynthesis. A) Schematic diagram of purine biosynthesis. Isotope tracing analysis performed with $^{14}$C glycine for de novo and $^3$H hypoxanthine for salvage pathway. B) RNAseq analysis revealed that IMPDH2 activity is significantly increased during therapy as compared to C) down regulation of salvage rate limiting enzyme APRT. D)$^{14}$C glycine incorporation via de novo synthesis of the DNA and RNA with or without TMZ therapy in the presence and absence of ARL13B. U251 GBM cells were pulsed for 6 h with $^{14}$C glycine, DNA and RNA were isolated, and $^{14}$C incorporation was measured by mass spectroscopy. E) $^3$H hypoxanthine incorporation via salvage pathway.
Figures 4B, 4C:
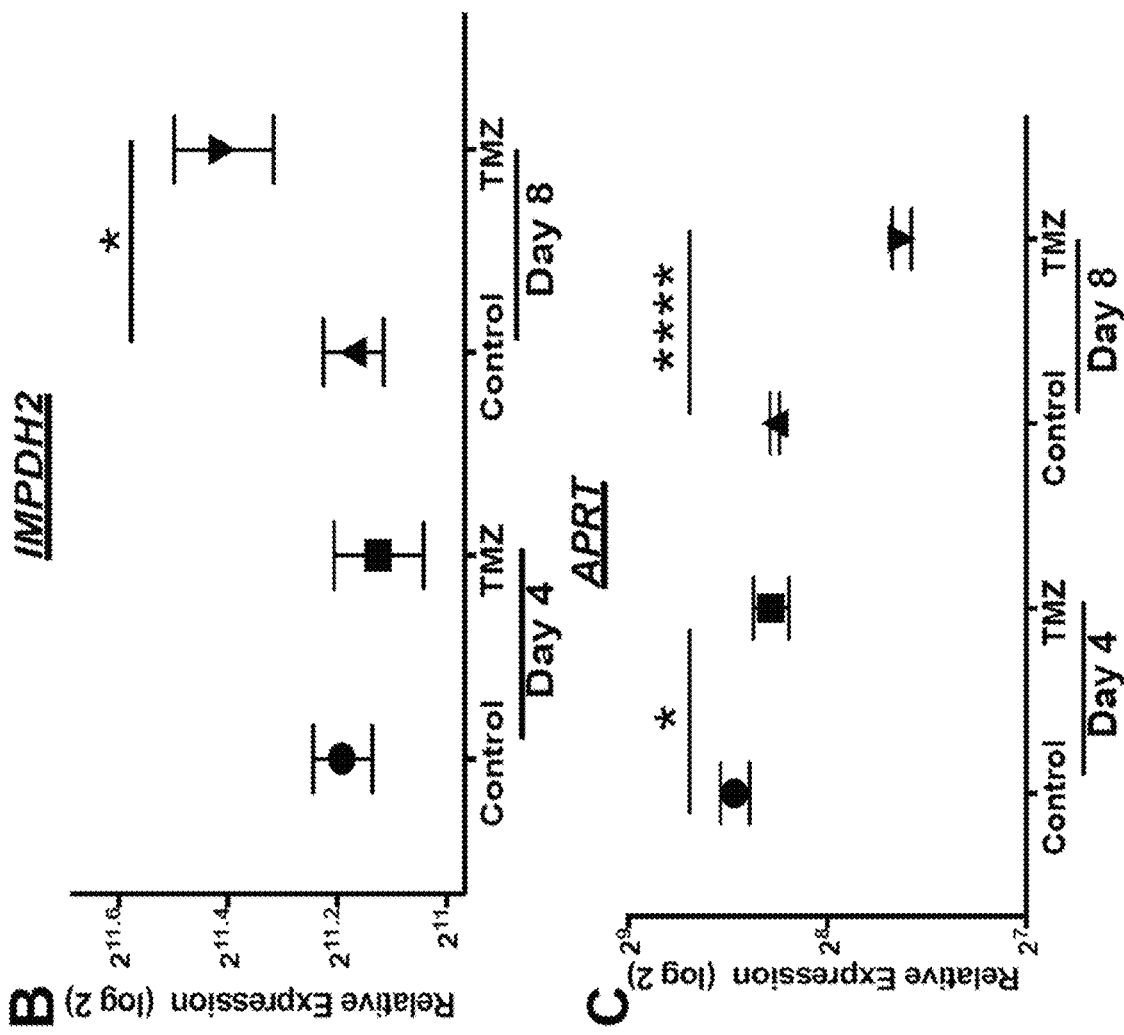
Figure 4D:
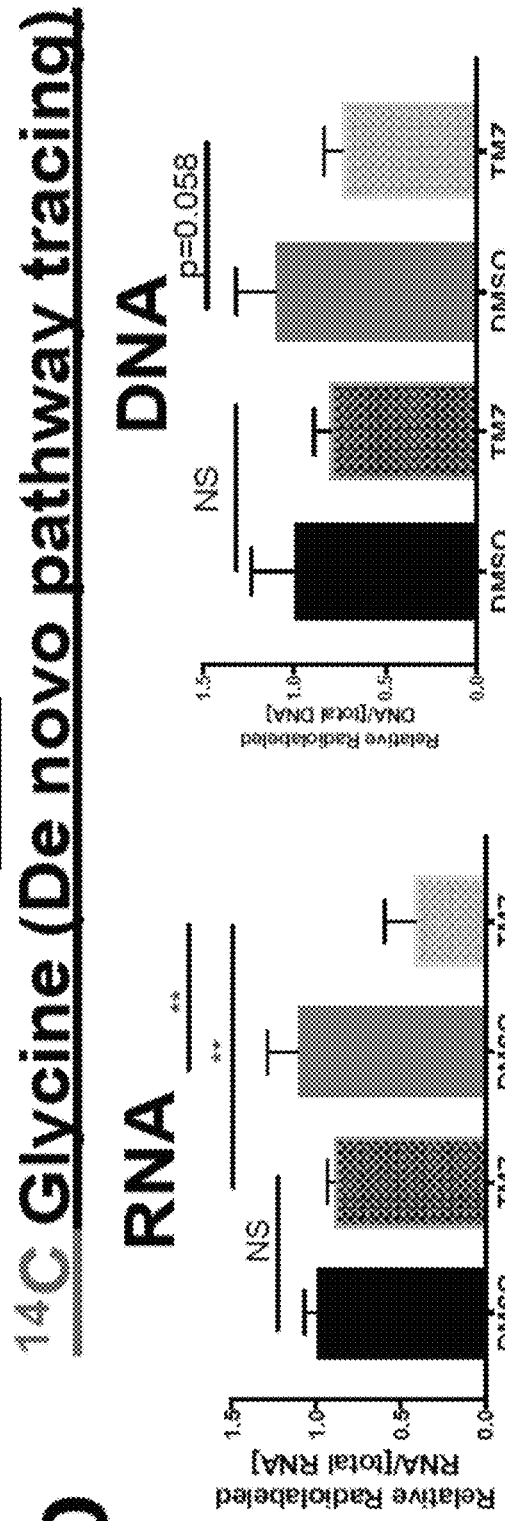
Figure 4E:
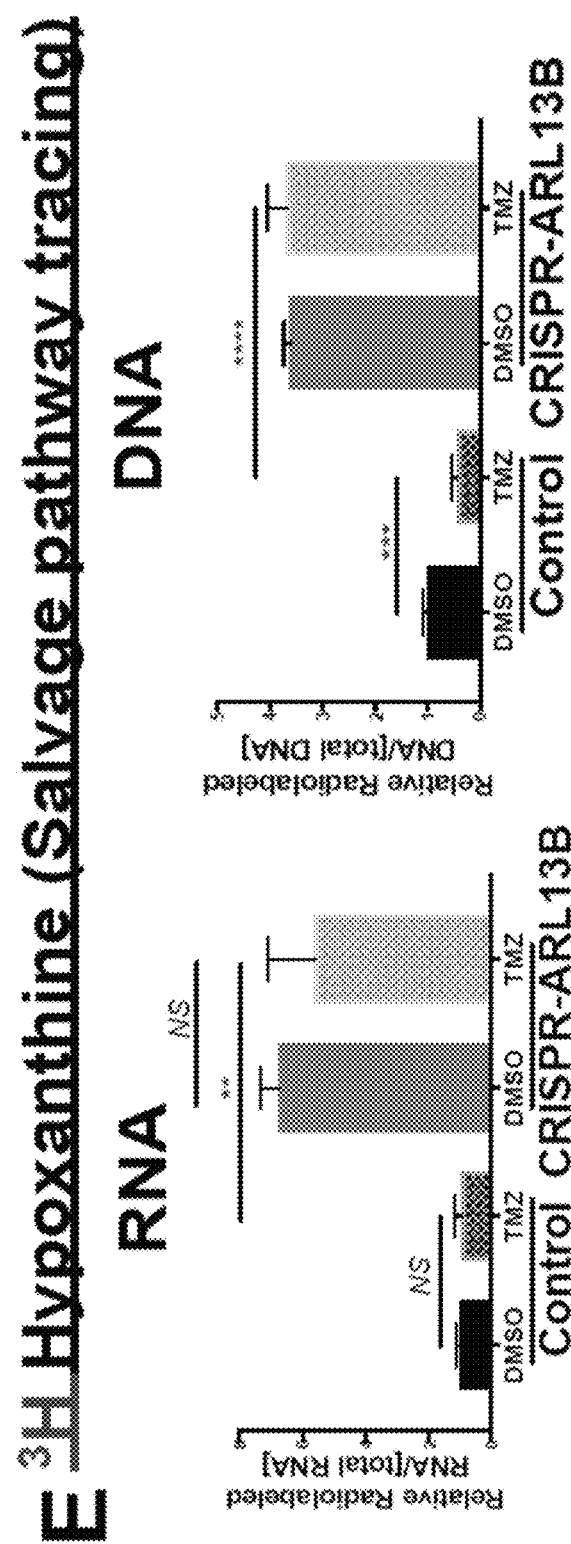

2.5. The ARL13B-IMPDH2 interaction during TMZ therapy alters the path to purine biosynthesis: IMPDH controls the gateway to purine nucleotides, by analyzing the rate-limiting reaction of de novo GTP biosynthesis at the inosine monophosphate (IMP) metabolic branch point[36] (FIG. 4A). This critical reaction appears to be present in every organism. Alternatively, purine bases, released by hydrolytic degradation of nucleic acids and nucleotides, can be salvaged and recycled. This is an energy-saving pathway for purine biosynthesis, and its inefficiency can result in many pathological conditions including Lesch-Nyhan syndrome[37]. In cancer, rapid cell division results in a high demand for purine nucleotides that generally cannot be sustained by salvage pathways, which may explain the importance of IMPDH in cancer[14, 38]. This information, combined with our finding of a direct interaction between ARL13B and IMPDH2 during TMZ therapy, allows us to postulate that such an interaction may be playing a role in regulation of purine biosynthesis pathway. To investigate further, we first performed [$^{14}$C]-glycine (de novo) and [$^{3}$H]-hypoxanthine (salvage) pulse-chase study during therapy, which allowed us to measure the activity of specific purine biosynthesis pathways[39] (FIG. 4A). During TMZ therapy, purine biosynthesis activity via the salvage pathway was reduced by about 50%, whereas the de novo pathway activity remained unchanged (FIGS. 4A-1 & 2). RNAseq analysis revealed that the majority of the rate-limiting enzymes for the de novo pathway were unchanged or unregulated (FIG. 4B & data not shown) and enzymes involved in salvage pathway were downregulated (FIG. 4C & data not shown). Next, to examine the role of ARL13B, we performed a similar pulse-chase experiment as described above in the CRISPR-mediated ARL13B knocked out cells and observed that in the absence of ARL13B, the de novo biosynthesis pathway activity was reduced significantly in a TMZ-specific manner (FIG. 4D). Moreover, removal or ARL13B enhanced the salvage activity about 5-fold (FIG. 4E, p<0.0005). Based on this, we conclude that ARL13B may act as a negative regulator for the salvage pathway and is play a role in therapy-induced switch of the purine biosynthesis.

Figures 5A, 5B:
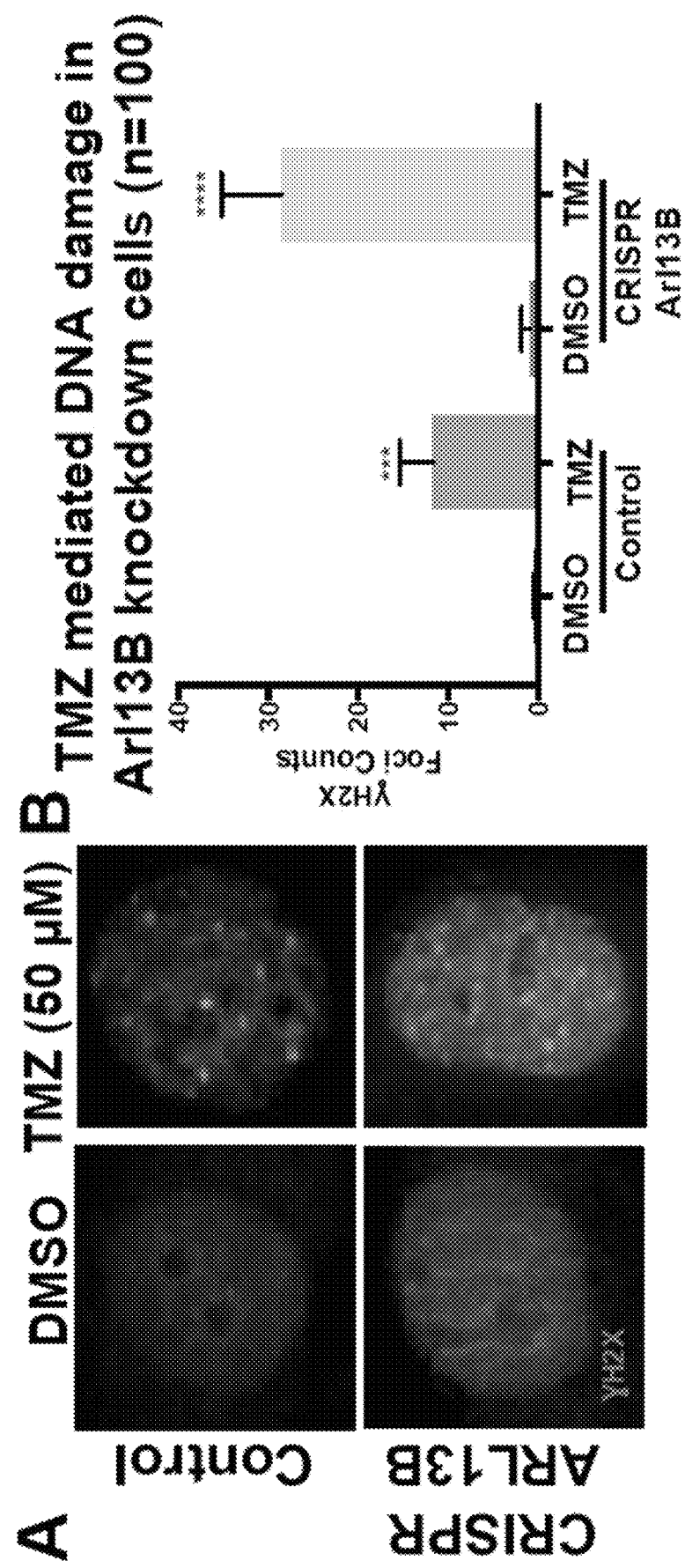
FIG. 5A-5D. Removal of ARL13B sensitizes GBM to TMZ therapy. A) Extent of DNA damage revealed by H2X foci. B) Quantitative measure of H2X foci of different conditions counted in 100 cells. C) and D) shRNA mediated knockdown of ARL13B PDX lines were implanted in the nu/nu mice intracranially. After tumor establishment (7 days post implantation measured by BLI) animals were treated with suboptimal dose of TMZ (2.5 mg/kg) for 5 consecutive days. Animals were monitored for endpoint survival. C) GBMS PDX which is a mesenchymal subtype and D) GBM6, a classical subtype.
Figure 5C:
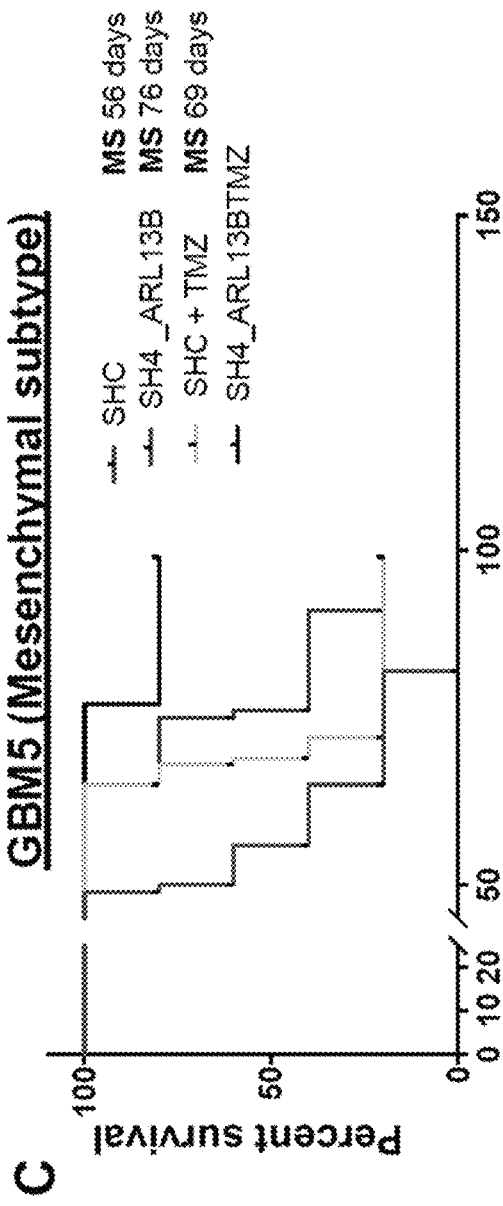

2.6. ARL13B KD enhances the therapeutic efficacy of TMZ both in vitro and in vivo: The monofunctional DNA-alkylating agent TMZ is a commonly used chemotherapeutic drug and the gold standard of treatment for GBM. Although the activity of the DNA repair enzyme O6-methylguanine-DNA methyltransferase (MGMT) has been identified as the critical modulator to determine the GBM sensitivity to TMZ, all GBMs, even those with MGMT inactivation, eventually stop responding to TMZ. This begs question whether an alternative mechanism of resistance may be involved in GBM. The anti-GBM activity of TMZ is predominately provoked by O6-methylguanine-DNA adducts. On the other hand, free purine bases, generated from the turnover of nucleotides in the tumor microenvironment, can be recycled via the salvage pathway. Based on this, we postulate that if ARL13B functions as negative regulator of the salvage pathway or is necessary for de novo purine biosynthesis, then removal of such a regulator will force the cells to recycle the alkylated guanine bases. As the cancer cells recycle and incorporate alkylated purines into their DNA, the damage should be induced and thus enhance the therapeutic efficacy of TMZ. To test this, we first treated the ARL13B knocked out lines with a physiological dose of TMZ (500$\mu$)[27, 28] in vitro and observed significantly elevated DNA damage measured by H2X foci (FIG. 5A-B). To evaluate this in vivo, two different subtypes of GBM (GBMS: MGMT methylated, GBM6: MGMT unmethylated[40]) were infected with lentivirus carrying shRNA against ARL13B and the knockdown cells were implanted intracranially. After tumor engraftment animals were treated with vehicle control or TMZ (2.5 mg/kg) for 5 consecutive days and animals were monitored by endpoint survival. We observed that ARL13B KD significantly sensitized PDX xenografts to TMZ therapy. The effect was most pronounced in the therapy resistance mesenchymal subtype[41] where 80% of animals in the group with ARL13B KO GBM treated with TMZ did not develop any tumor (FIG. 5C). In the classical subtype of GBM6, we observed 39% improvement in overall survival compared to control. Taken together, we conclude that ARL13B is necessary for chemotherapeutic adaptation and could be a novel target to overcome chemoresistance in GBM.

2.7. Summary of preliminary data: Our preliminary data allows us to draw the following conclusions:

- The PRC2 complex catalytic subunit EZH2 is critical for adaptation to alkylating-based anti-GBM chemotherapy.
- EZH2-mediated adaptation to TMZ is independent of its methyltransferase activity.
- ARL13B, a ciliary protein, is a downstream target of EZH2 and its expression is regulated via a non-canonical function of EZH2 during TMZ therapy.
- ARL13B expression in GBM cells is predominately localized in the cilia, and the length of cilia is significantly increased in GBM cells during TMZ therapy.
- Knockdown of ARL13B significantly inhibits GBM growth in the orthotopic PDX GBM model.
- ARL13B can directly interact with IMPDH2, a rate-limiting enzyme for the purine biosynthesis pathway.
- During TMZ therapy, salvage activity for purine biosynthesis was reduced by about 50%, but therapy did not alter the de novo synthesis pathway, indicating that during chemotherapy GBM cells may relies on the de nova pathway for purine biosynthesis.
- Removal of ARL13B resulted in a 6-fold increase in the salvage pathway and about a 50% decrease in the de novo pathway in a TMZ-specific manner.
- shRNA-mediated knockdown of ARL13B increased TMZ-mediated DNA damage and enhanced the therapeutic efficacy of TMZ in the orthotopic PDX model of GBM.

3. Significant & Innovation:

3.1. Hypothesis

Figure 6:
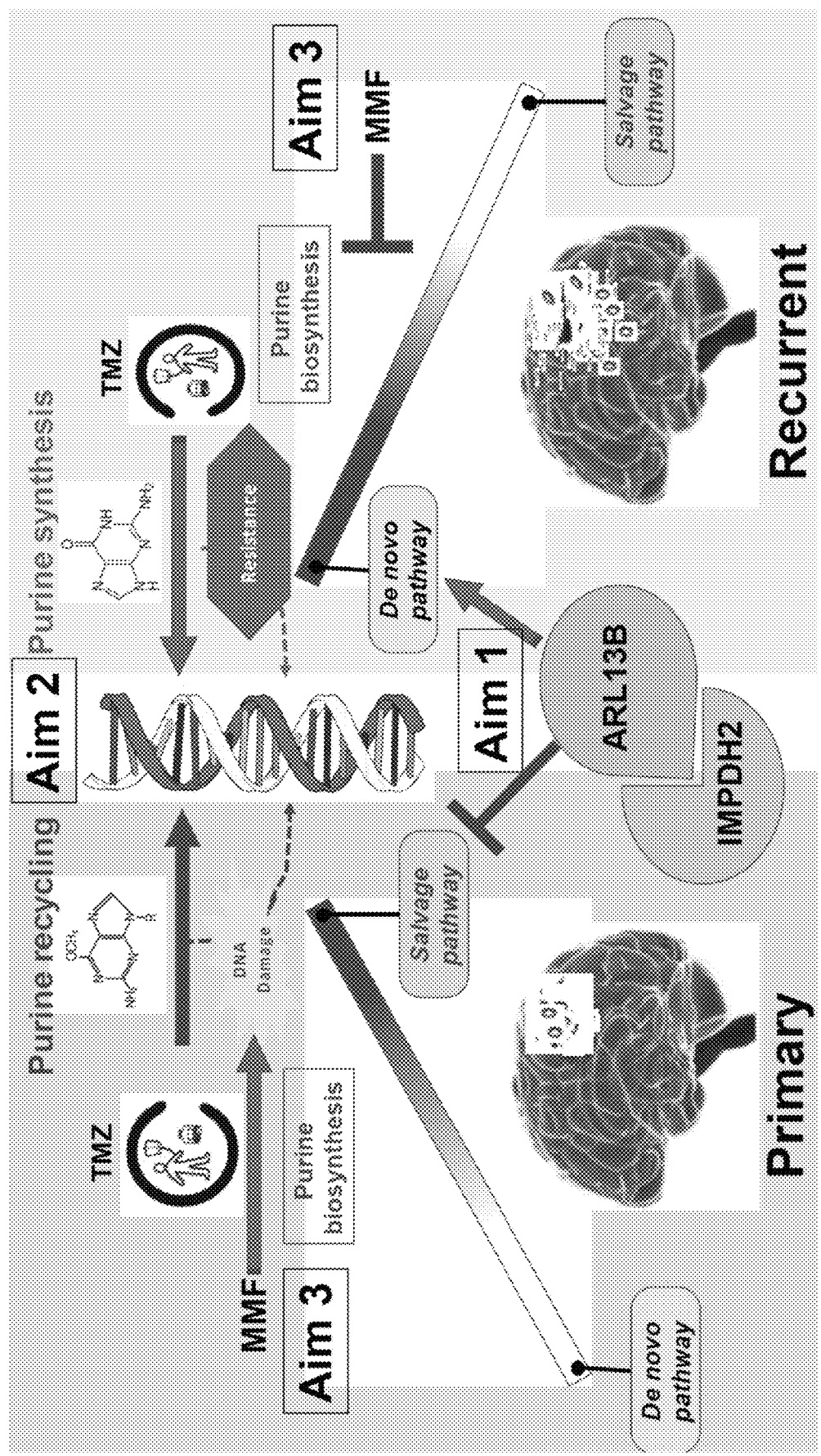
FIG. 6. Schematic diagram of proposed hypothesis. Aim 1 will examine how ARL13B-MPDH2 interaction will influence different purine biosynthesis pathways. Aim 2 will elucidate the role of purine metabolism in promoting resistance in GBM. Aim 3 will try to regulate purine biosynthesis in order to prevent therapeutic resistance and recurrence in GBM.

Based on our preliminary data, we are hypothesizing that ARL13B functions as a regulator of the purine biosynthesis pathway and its activity is necessary for therapeutic adaptation in GBM (FIG. 6). We believe that during alkylating-based chemotherapy, EZH2-mediated upregulation of ARL13B enhances the ARL13B-IMPDH2 interaction. We are proposing that such an interaction may lead to two possible outcomes: i) augment the activity of the de novo purine biosynthesis pathway, or ii) inhibition of the salvage recycling of nucleotides from the microenvironment. Either of these outcomes could lead to the development of resistance against the alkylating chemotherapy by allowing the cancer cells to support their nucleotide demand via the de novo pathway. Most importantly, this switch may allow the GBM cells to circumvent their dependency on the salvage pathway, thus enabling them to avoid recycling of the alkylated nucleotides during chemotherapy and thus evade chemotherapy-induced DNA damage. We believe that this mode of purine biosynthesis regulation may be a novel mechanism of resistance, which could be targeted to prevent GBM recurrence by sensitizing the GBM cells to conventional BBB permeable alkylating chemotherapy.

3.2. Significance:

1) Glioblastoma is one of the most lethal cancers. Last year in US, 2-3 individuals were diagnosed with GBM every hour. Despite decades of research, and with the most aggressive standard of care against any cancer, only 10% of patients with GBM will survive more than 5 years and, thus very much in need of effective therapies[42].

2) Therapeutic resistance is one of the major causes of recurrence in GBM. Nearly 100% of GBMs will eventually recur despite aggressive therapy. Furthermore, upon recurrence tumors are more aggressive, infiltrative and resistant to nearly all currently available therapies. This inevitable recurrence demands rigorous study focused on elucidating the mechanism of therapeutic resistance in order to provide effective treatment[1, 43].

3) Available chemotherapeutics against GBM is limited. The current chemotherapeutic arsenal is hampered by the blood-brain-barrier (BBB). Temozolomide (TMZ), an alkylating chemotherapeutic, is one of few available drugs to show both BBB penetrance as well as active against GBM. Augmenting the efficacy of this already proven chemotherapeutic will be the quickest way to ensure meaningful progress towards GBM treatment.

4) Identification of a novel purine metabolism regulator that can contribute to resistance will facilitate the development of innovative therapeutics against GBM. Purines are the building blocks for DNA and RNA and therefore play an essential role in uncontrolled cellular proliferation in cancer. Alkylating-based chemotherapies such as TMZ or BCNU are an approved part of the standard care for many cancers including GBM. If the regulation of purine biosynthesis plays a role in promoting resistance, then inhibiting such regulation may provide a novel strategy to combat resistance.

5) If the proposed hypothesis is established in preclinical study, it could smoothly be translated into the clinic since there are multiple FDA approved drugs to target IMPDH2 already available. The key finding of our proposal is that the interaction between ARL13B and IMPDH2 allows GBM cells to resist alkylating-based chemotherapy. IMPDH2 is a key rate-limiting enzyme for purine biosynthesis and has been extensively evaluated as a drug target for various pathological conditions including viral infection and inflammation[44, 45]. Most importantly, some of the IMPDH2 inhibitors such as CellCept have already been approved by FDA and thus could easily be tested in a new clinical trial for GBM or even for other cancers[46].

3.3. Innovation:

1) Understanding therapeutic resistance is key to improving clinical outcomes for GBM patients. There is no consensus in the literature on the mechanisms behind chemoresistance in GBM. To date, MGMT is the most established modulator of resistance to TMZ[47]. However, almost all patients eventually fall into relapse irrespective of their MGMT status, confirming that this cannot be the only driver of resistance. Critically, alternative cause of therapeutic resistance needs to be explored in order to improve clinical outcomes for GBM.

2) The regulation of purine biosynthesis via ARL13B-IMPDH2 interaction is novel and will establish a new paradigm in the regulation of purine biosynthesis and metabolomics in general. Even though purine metabolism is a fundamental process in all living organisms, the direct mechanisms behind how cells regulate/choose different pathway to synthesize purine is largely unknown. In this proposal, we set to examine a novel regulator that allows the cells to control specific pathways for purine biosynthesis.

3) A likely mechanism of chemoresistance for the cancer stem cell model. A previous report showed that the therapy-resistant CSC population in GBM preferentially utilizes the de novo biosynthesis pathway[12]. Taken together with our observations, it is probable that the de novo pathway may allow GBM CSCs' to avoid salvage-pathway-mediated incorporation of alkylated purines during TMZ therapy thus avoiding the chemo-activity and promoting resistance. Disrupting the AR13B-IMPDH2 interaction may provide a novel actionable target to prevent CSC-mediated chemoresistance.

5) Therapeutically targeting the purine biosynthesis pathway via IMPDH2 to overcome chemoresistance may be less toxic to normal tissues, specifically for GBM since it has been previously reported that the IMPDH2 activity in GBM tissues was 4-fold higher than in the surrounding normal brain tissue[11].

6) Preclinical studies targeting chemoresistance through regulation of purine metabolism may lead to a useful therapeutic paradigm in other cancers. Because purine biosynthesis is indispensable for all rapidly dividing cells, it is a ubiquitous hallmark of cancers. Furthermore, the effective use of alkylating agents as the first-line therapeutics means that better understanding of this process of alkylated nucleotide salvage and incorporation could have a wide impact in numerous cancer types.

In summary, the proposed research is innovative in several aspects including novel mechanisms, unique, actionable targets, availability of FDA approved inhibitor, effective experimental design, synergistic targeting strategies, and utilization of state-of-the-art technology to search for an effective therapeutic intervention of a disease that badly need a breakthrough.

4. Approach

Scientific Rigor and Reproducibility: We will employ robust and unbiased scientific methods to our experimental design, methodology, analysis, interpretation, and reporting of results. We will evaluate cellular responses of at least three independent biological replicates for each experiment. The preclinical evaluation of any experimental therapeutics will be tested in all three subtypes of the GBM PDX model to ensure generalizability.

Sex and other biological variables: To examine if sex influences the patient-derived GBM model's (PDX) response to modulation of purine biosynthesis regulation and its role in chemoresistance, we will interrogate biological response for both male and female-derived PDX as we as mice and report the results separately.

Aim 1: To Investigate the Role of Ciliary Protein ARL13B in Regulating Purine Metabolism.

Rationale: The foundation of this proposal builds on our novel finding that a ciliary protein ARL13B can physically interact with IMPDH2, a key rate-limiting enzyme for purine biosynthesis (FIG. 3). Loss of ARL13B in GBM cells not only alters the method cells employ for purine production, but also confers susceptibility to alkylating-based chemotherapy such as TMZ. Based on these observations, our primary goal is to perform a comprehensive investigation of the role of ARL13B in purine metabolism by conducting the following experiments.

1.a. Validate the ARL13B IMPDH2 interaction in different subtype of GBMs in vivo and in freshly isolated GBM tissues: To investigate the interaction between IMPDH2 and ARL13B in vivo, we will first establish the orthotopic tumors using at least 2 different PDX lines from each molecular subtype of GBM. We have an active collaboration with Dr. David James, one of the leading experts in patient-derived xenograft (PDX) models for neurological malignancies and have access to 22 well-characterized PDX GBM lines derived from all three subtypes of GBM[48]. The tumor growth can be monitored using bioluminescence imaging (BLI) as these PDX lines have stably expressed luciferase genes. Once the tumors are established, animals will be divided into two groups (n=18) and will be treated with or without TMZ (2.5 mg/kg) for 5 consecutive days according to an established protocol[49, 50]. Animals will be sacrificed at the following time points: i) when mice show signs of significant disease burden without any therapy (n=6), ii) post-therapy recurrence (n=6), and iii) during therapy (n=6, after 3 days post-TMZ therapy). We believe that these 3 time points is necessary to capture realistic view of tumor evolution as the path to fitness is very dynamic process. After being sacrificed at the above time points, brains from three mice from each group will be harvested and subject to various immunostaining analysis including i) immunofluorescent analysis to investigate the expression and colocalization of ARL13B and IMPDH2 during and post therapy; ii) in situ proximity ligation assay (PLA), which is a method to detect the interaction between ARL13B and IMPDH2 in fixed tissue (ThermoFisher) during therapy (n=6, after 3 days post-TMZ therapy)[51]. The specific interaction between these two proteins can be measured by using the corresponding two primary antibodies raised in different species (ab136648, ab129165) followed by species-specific secondary antibodies with PLA probes, which will only generate a detectable fluorescent signal if two probes are in close proximity (<40 nm). This powerful technique will allow us to validate our Co-IP results further and semi quantitatively assessment of how the TMZ therapy influences this interaction in a clinically relevant in vivo PDX model. Next, to investigate the thermodynamic and kinetic parameters of the ARL13B-IMPDH2 interaction, we are proposing to employ surface plasmon resonance (SPR), which measures the change in surface refractive index of a solvent near a surface (usually a gold film) that occurs during protein-protein complex formation and dissociation[52]. For this purpose, purified recombinant ARL13B and IMPHD2 will be purchased from Novus (Abingdon, UK). Biacore T200 (GE Healthcare, USA) will be used for real-time binding interaction studies at the Kech Biophysics Facility, Northwestern University, according to a previously published protocol[53]. The equilibrium dissociation constant (KD) for the individual proteins will be obtained to evaluate the binding affinity by using the BIAEvaluation 2.0 software (GE Healthcare). Such knowledge of association and dissociation parameter, as well as the binding constant, will be critical for measuring the ARL13B-IMPDH2 interaction quantitatively.

Mammals have two IMPDH isoforms, encoding IMPDH1 and IMPDH2, both contain 514 residues[36, 54]. These two isoforms are 84% identical and almost indistinguishable in their kinetic properties. IMPDH1 is typically expressed constitutively at low levels, while IMPDH2 is amplified during proliferation and transformation. Thus, it is imperative that we examine the selectivity of ARL13B interaction. We will conduct Co-IP experiments as described above (Section 2.4). If ARL13B physically interacts with both isoforms, then we will examine which interaction is critical for regulation of purine biosynthesis during chemotherapy by generating loss and gain of function for both isotypes using CRISPR technology in order to evaluate the purine biosynthesis during TMZ therapy (as described in Section 2.5).

Figure 7:
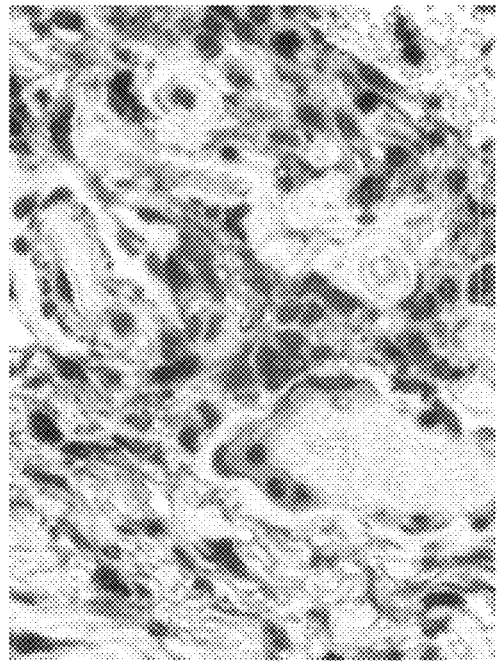
FIG. 7. Immunohistochemical analysis of matched primary and recurrent GBM tissue for ARL13B expression.
Figure 7:
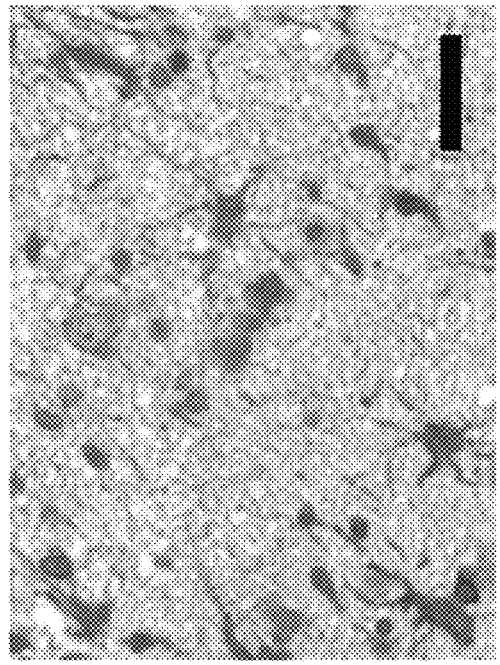
Figure 7:
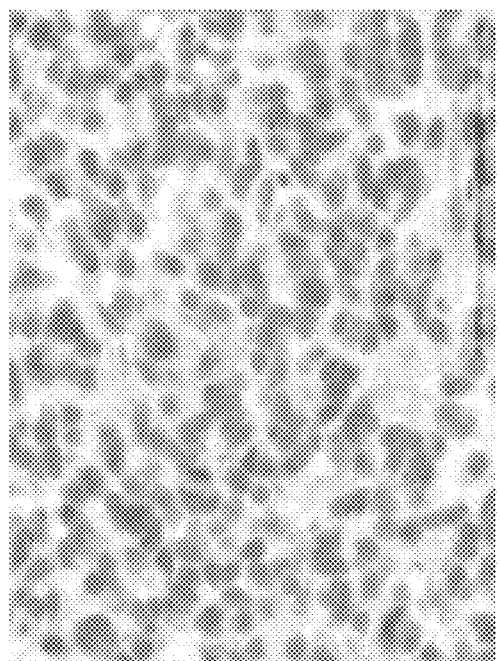
Figure 7:
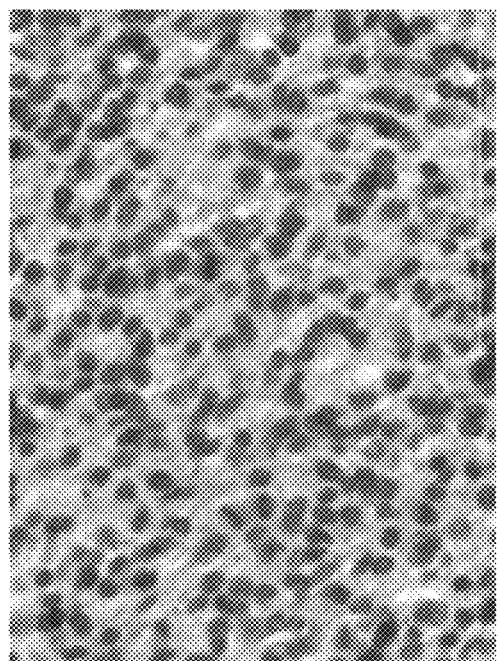

To validate the ARL13B-IMPDH2 interaction clinically, we will perform Co-IP experiments in freshly isolated tissues from 3-5 GBM patients. For clinical samples, we have an active collaboration with the Co-I for this grant, Dr. Craig Horbinski, MD, Ph.D., a neuropathologist and Director of the Northwestern Nervous System Tumor Bank. The sample will be collected from patients undergoing surgery under an approved protocol (STU00095863) after obtaining informed consent. Biospecimens used in this study will be subject to a de-identification process, and all protected health information (PHI) will be removed before the sample is processed. A single cell suspension will be created by using a Brain Tumor Dissociation Kit, and the immune cells will be excluded by CD45 negative selection kit (Miltenyi Biotech), samples will then be subject to bidirectional IP as described above. This will validate the ARL13B-IMPDH2 interaction clinically. Next, using a collection of over 30 matched primary and recurrent GBM tissues from the Northwestern Nervous System Tumor Bank, we will examine ARL13B expression changes in primary and recurrent tumors. Having already explored the staining in some of these samples we were able to visualize a striking difference in ARL13B staining and tissue architecture between primary and recurrent samples (FIG. 7) and we believe that the proposed experiments will shed light on the role of ARL13B.

Figures 8A, 8B:
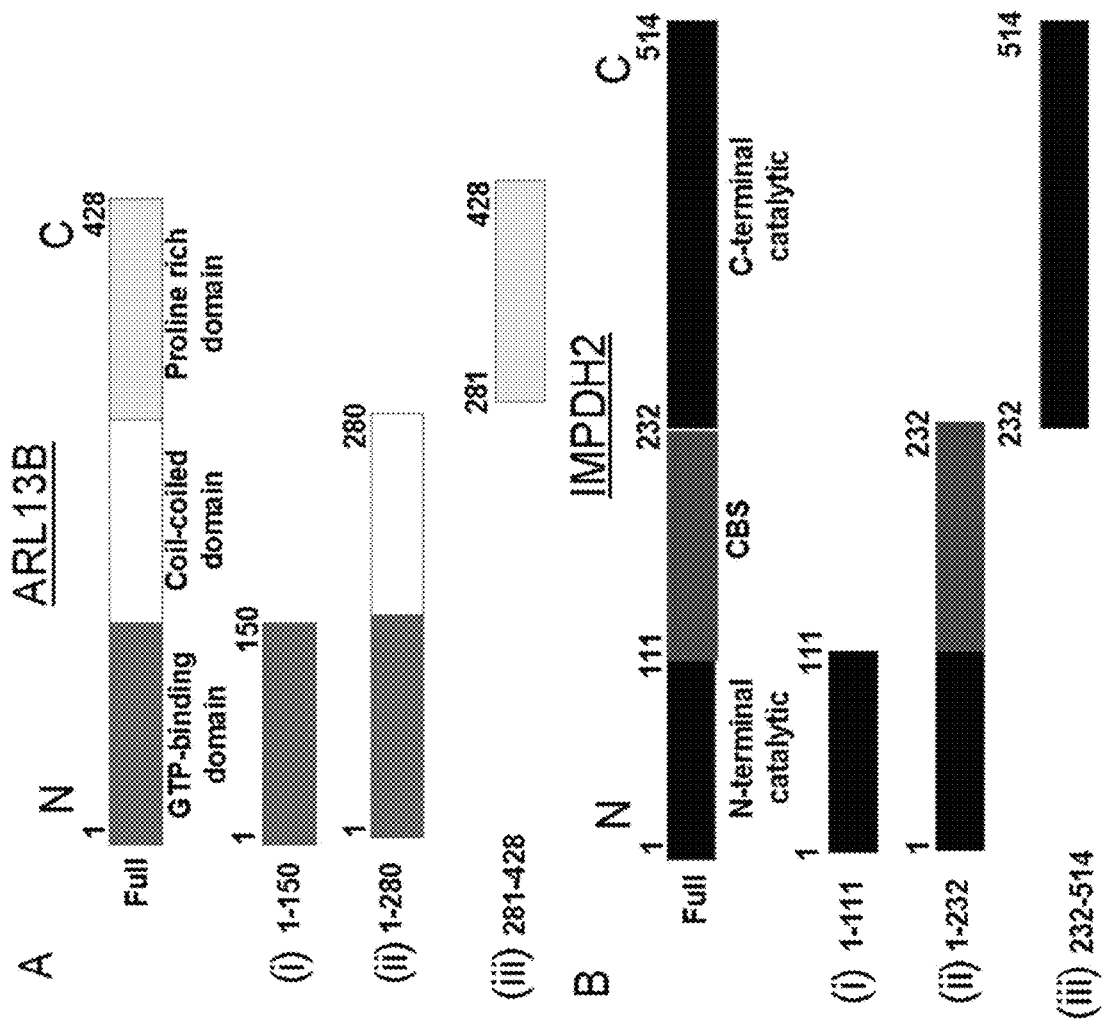
FIG. 8A-8B. Schematic diagram of A) ARL13B critical domains and B) IMPDH2 critical domain.

1.b. Mapping the domains necessary for the ARL13B-IMPDH2 interaction: To elucidate the physiological role of the ARL13B-IMPDH2 interaction, we will map out the interacting domains. Human ARL13B is a ciliary GTPase which has 3 major domains: i) GTP-binding domain (N-terminus, 1-150 aa), ii) coil-coiled domain (150-280 aa) and iii) proline-rich domain (C-terminus, 280-428 aa) (FIG. 8A)[55]. The biological function of the N-terminus GTPase is critical since 3 missense mutations in this domain can result in pathological conditions such as Joubert syndrome. IMPDH2, on the other hand, has two domains: the catalytic domain that contains its active site in the loops on the C-terminal ends, and a subdomain containing two CBS (cystathionine-beta-synthatase) domains (FIG. 8B)[36]. To identify the domains that are involved in the ARL13B-IMPDH2 interaction, we will generate His-tagged constructs of various domains of ARL13B as described in FIG. 8A and Flag-tagged constructs of the various domains of IMPDH2 (FIG. 8B). These constructs will be co-transfected in Hek 293T cells, and Co-IP will be performed with the corresponding antibody to map out interaction. Next, we will identify the specific area (10-20 aa) of this domain responsible for this interaction by generating deletion constructs using CRISPR technology. The information generated will be critical for enhancing our understanding of the ARL13B-IMPDH2 interaction and may allow us to design/screen inhibitors to prevent this interaction.

1.c. Role of the ARL13B-IMPDH2 interaction in purine biosynthesis: CRISPR-mediated knockout of ARL13B directly impacts which pathway GBM cells choose to synthesize purines (FIG. 4), and we have identified IMPDH2 as one of the significant interacting partners of ARL13B during TMZ therapy. Based on this, we set out to investigate the mechanisms of ARL13B-mediated regulation of purine biosynthesis. First, we will examine if ARL13B can alter purine biosynthesis in all three subtypes of PDX GBM lines by performing a pulse-chase study during TMZ-therapy. We will measure the incorporation of $[^{14}C]$-glycine (de novo) and $[^{3}H]$-hypoxanthine (salvage) into RNA and DNA as described by Ben-Sahra et al[39,56]. Next, we will examine the total metabolites in all different subtypes with or without TMZ therapy as described in Huang et al[57].

To further investigate the role of ARL13B in purine metabolism, we will emply a loss-of-function model by using shRNA and CRISPR and a gain-of-function model by overexpressing ARL13B in all three subtypes of GBM. With these models, we will conduct the incorporation and total metabolomics experiments as described above. We have established an active collaboration with Issam Ben-Sahra, Ph.D., an expert in purine metabolism and Co-I for this proposal. His lab has extensive experience in performing experiments to study purine metabolism[39,56]. These are essential experiments to not only examine the role of ARL13B in different subtypes, but also to investigate if the specific subtypes can influence the path to purine biosynthesis in GBMs.

Next, to examine the role of ARL13B in purine biosynthesis pathways in vivo, orthotopic PDX GBM tumors will be established according to our established protocol[49,50]. During tumor implantation, we will place an intracerebroventricular cannula, which will allow us to inject $^{13}C_2$-Glutamine (CIL, MA) and $^{13}C_5$-hypoxanthine (CIL, MA) directly into the tumor to achieve more effective labeling[58,59]. A 26-gauge single acute guide cannula (Plastic One, Roanoke, Va.) will be implanted into the same bar hole where the PDX cells will be injected in the brain (0.22 mm posterior, 1.0 mm lateral and 2.3 mm ventral to bregma). All cannulated mice will be given 1 week of postoperative recovery which will also allow the tumor xenograft to be established. During this time mice will be handled daily to minimize nonspecific stress. After ensuring tumor establishment via BLI, we will inject the stable isotope labeled amino acid intratumorally according to a published protocol[57,60]. The $^{13}C_2$-glutamine (0.3 mg/ml) and $^{13}C_5$-hypoxanthine (2 mg/ml) will be dissolved in artificial cerebrospinal fluid (Harvard Apparatus) and will be injected in the same tumor implantation coordinate using a stereotactic frame in a total volume of 2-5 µl with a Hamilton syringe (2 injections, 24 h apart). 24 h after the last injection, animals will be sacrificed, brains will be harvested, and human tumor cells will be isolated using a commercially available kit (Miltenyi Biotech). Tumor cells will be isolated from at least 3 mice for the following groups: i) control vehicle (DMSO) treated, ii) TMZ treated (2 mg/kg for 3 days), iii) post-TMZ recurrent tumor[49] iv) shRNA control tumor and v) ARL13B KD tumor (inducible shRNA system). After isolation, we will conduct the incorporation assay as well as total metabolomics workup as described above[39,56].

To investigate if ARL13B is required for IMPDH activity, we will employ a commercially available IMPDH activity assay kit (BMR, NY) to quantitatively measure the IMPDH activity during TMZ therapy. The CRISPR-mediated ARL13B KO GBM cells will be employed to investigate if ARL13B is necessary for IMPDH activity. To examine if the interacting domain alone is sufficient for IMPDH activity we will reconstitute ARL13B KO cells with various domains of ARL13B as described in section 1b and measure the IMPDH activity during therapy. This may allow us to identify the active domain of ARL13B that may be necessary for purine biosynthesis. Finally, to investigate if the ARL13B interaction specificity towards different isoforms of IMPDH and its biological consequence, we will generate an CRISPR-mediated knockdown of IMPDH 1 or 2 GBM cells and measure the IMPDH activity during therapy. We believe that these experiments will provide us with the evidence necessary for understanding the role of the ARL13B-IMPDH2 interaction in purine biosynthesis.

Data collection, analysis, statistical analysis, and power considerations: In general, data will be described as mean (SD) for continuous variables, and number (percentage) for categorical variables. Statistical analyses will be performed using SAS9.4 (SAS Institute Inc., Cary, N.C.) and GraphPad Prism5.0 (GraphPad Software Inc, La Jolla, Calif.). P-values or Benjamini-Hochberg adjusted false discovery rates less than 0.05 will be considered as significant. All the SPR reactions the reflectivity of each spot was altered when the protein samples will be binding to the immobilizing proteins. Percent change in reflectivity (% ΔR) will be calculated from the CCD signal and normalized by subtracting the reflectivity for the same concentration of normal human IgG. Data will be processed and analyzed using Scrubber-Gen (HORIBA France). For measuring the isotope-labeled nucleotide incorporation, an incorporation rate of 30% was observed in our pilot experiment. Based on this result, we will have 80% power at an alpha level of 0.05 to detect a difference of incorporation rate between treated and untreated groups with 24 animals. McNemar's test will be conducted Anticipated results and interpretation: Based on our preliminary data we expect the ARL13B-IMPDH2 interaction to be validated across all GBM subtypes. However, the extent of interaction could vary between different subtypes. We cannot predict if this interaction will be validated clinically via IF analysis since such a technique could be difficult to perform in the paraffin fixed tissue. We expect to identify interaction domains between the two proteins which will allow us to identify or design specific inhibitors for therapeutic purpose. We believe that ARL13B may not influence the IMPDH enzymatic activity but rather the ability of the cells to use the de novo vs. salvage pathway and in this case identification of the binding motif will be critical.

Potential Pitfalls and Alternative Approaches: The experiments proposed in this aim are directly aligned with the collective expertise of the Ahmed and Ben-Sahra laboratories, so we do not expect significant technique difficulties arising from these studies. Some of the possible challenges and alternatives are as follows: What if we observe GBM subtype-specific variability in regulating purine biosynthesis via ARL13B? As different subtypes of GBM show differently susceptibility to TMZ, we expect to see difference in the role of ARL13B-mediated purine synthesis regulation. If we observe a significant difference, we intend to investigate if such a difference may be responsible for variable TMZ susceptibility.[61] What if the IF analysis fails to validate the ARL13B-IMPDH2 co-localize in the clinical samples? IF analysis is extremely challenging to perform in the paraffin fixed tissue. As an alternative, we will perform IP analysis on the freshly isolated GBM tissue.

Summary: Collectively, utilizing the interaction dynamics with the domain mapping will allow to elucidate the role of ARL13B-mediated regulation of purine metabolism and provide us with a deeper understanding of how purine biosynthesis is involved in promoting therapeutic resistance in GBM.

Aim 2: To Elucidate the Role of Purine Metabolism in Promoting Resistance to TMZ Rationale: Based on our preliminary data, we are proposing that in GBM, TMZ-mediated therapeutic stress can alter the pathway that GBM cells choose to supplement their need for purines (FIG. 4). The role of purine biosynthesis in promoting resistance to alkylating-based chemotherapy is yet to be investigated. We are proposing a novel hypothesis that GBM cells switch from salvage to de novo pathway during TMZ therapy to prevent recycling the alkylated nucleotides thereby resisting the chemotherapy-induced DNA damage. Thus, our goal for this specific aim is to investigate if the regulation of purine biosynthesis is necessary for promoting chemoresistance in GBM.

Figure 9A:
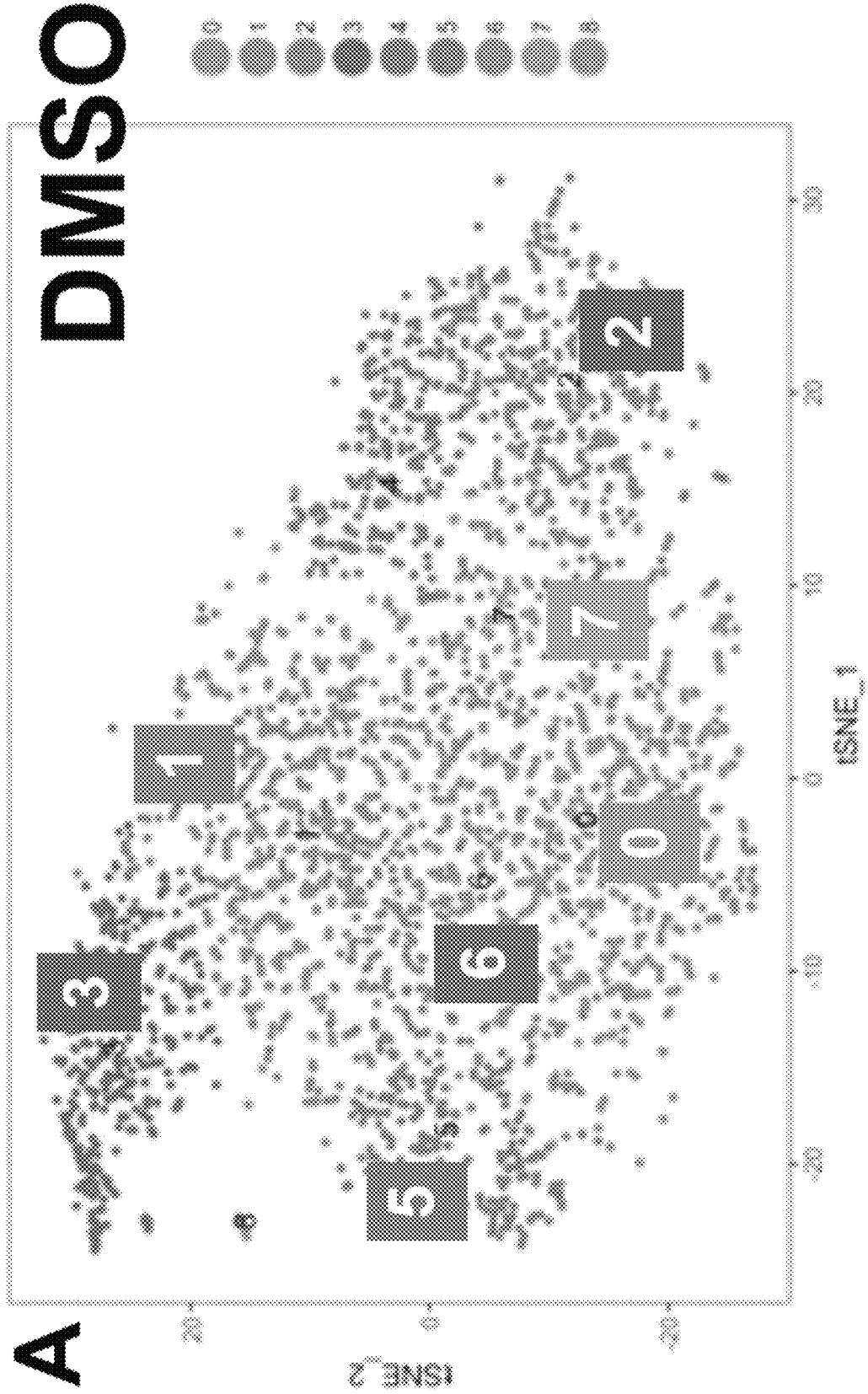
FIG. 9A-9D. Single cell transcriptome analysis in post TMZ orthotopic recurrent PDX GBM43 model. tSEN map of orthotopic PDX GBM43 treated with A) Vehicle (DMSO) or B) TMZ (2.5 mg/kg) and analyzed when mice show signs of disease burden. C) Waterfall plot showing the cells in different tSNE clusters with purine biosynthesis pathway related gene expression and D) ARL13B expression demonstrating cluster 1 and 2 with elevated expression.
Figure 9B:
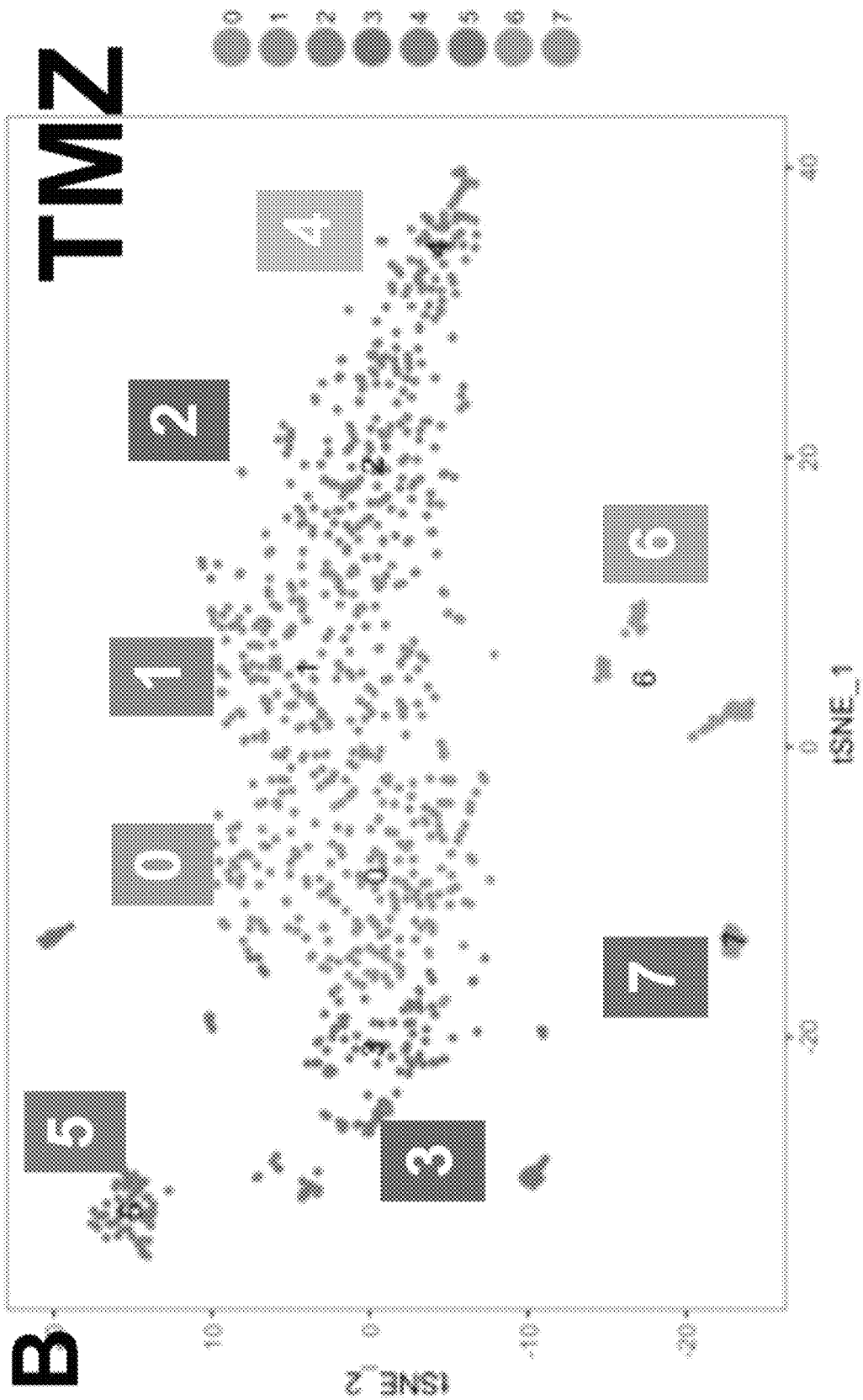

2.a. To examine if alkylated nucleotides can be recycling via the salvage pathway: TMZ is a monofunctional alkylating agent that can methylate nitrogen atoms in the DNA ring and the extracyclic oxygen group. The common site of methylation is at the N7 position of guanine (N7-MeG, 60-80%), followed by the N3 position of adenine (N3-MeG, 10-20%) and the 06 position of guanine (O6-MeG, 5-10%)[62]. Even though, the 06 is the least frequent alkylated DNA adduct, is it responsible for the majority of the cytotoxicity during TMZ therapy. Our brain predominately relies on circulating free nucleosides for the synthesis of new nucleotides, RNA and DNA[63, 64]. In neural tissue, the salvage pathway plays a critical role in maintaining the nucleotide balance, and the utilization of de novo pathways diminish towards adulthood. Even with CNS pathology like GBM, the activity of the rate-limiting enzymes of the salvage pathway is significantly higher than the de novo pathway[11]. This is partly due to the energy required for deriving the de novo pathway. However, it is not known how these different pathways of purine biosynthesis can influence the therapeutic outcome of alkylating-based chemotherapy such as TMZ. Notably, the salvage pathway can recycle the nucleosides/nucleobases from the DNA breakdowns of the dying cells and incorporate them into newly synthesized DNA[65]. We have observed that ARL13B KD cells show more DNA damage during TMZ therapy (FIG. 5) and our tracing analysis revealed that without ARL13B the activity of the salvage pathway was significantly elevated (FIG. 4). So, one possible explanation may be activated salvage pathway incorporating more alkylated nucleotides thus causing DNA damage. However, free nucleotides with specific modification (epigenetic) can be difficult to recycle and incorporate into newly synthesized DNA[66, 67]. Now the question is if GBM cells can salvage the alkylated nucleotide adducts and what happens if such adducts are incorporated in the DNA? To examine this question, we are synthesizing the O6-MeG with the help of Medicinal and Synthetic Chemistry Core Facility, Northwestern University (FIG. 9, see LOS). Once the O6-MeG is synthesized, multiple MGMT promoter methylated PDX lines will be treated with O6mG with the notion that if such alkylated addict can be salvaged and incorporated in DNA, it should cause DNA damage. This damaged DNA then will be quantified by γH2AX foci and Comet assay (CellBioLabs, CA) (FIG. 5A-B). Unmodified Guanosine analog (Sigma) will be used as a negative control, and TMZ will be used as a positive control. To be certain that the free alkylated nucleotides recycled and incorporated into the newly synthesize nucleotides, we will next treat the GBM cells with deuterium labeled $^2$H-O6mG) (CIL, UK). The incorporation of the stable isotope O6mG in nucleotides and DNA will be measured according to the published protocols[39, 56]. These data will allow us to assess if the TMZ mediated alkylated nucleotides can be recycled via the salvage pathway and incorporate into DNA.

2.b. Investigating the role of purine biosynthesis in promoting resistance to alkylating-based chemotherapy: If hyperactivation of de novo pathway enables cells to avoid the recycling of the alkylated purine during TMZ therapy, then generating loss or gain of function of this pathway will allow us to regulate GBM cells' response to TMZ therapy. To investigate that, two key rate-limiting enzymes for the de novo pathway, IMPHD2 and glycinamide ribonucleotide formyltransferase (GART), will be targeted to create inducible overexpression (clontech) and knockdown lines via inducible lentivirus shRNA (Genecopoeia) or cDNA expression in all three subtypes of PDX GBM. The hyperactivation or suppression of de novo pathway via loss or gain of function system will be validated by western blot and stable isotope incorporation study as described in section 1.c. These modified PDX lines can be tested for their ability to respond to alkylating based chemotherapy such as TMZ and Carmustine (BCNU), which will be examined by cell viability or DNA damage response assay. We will also generate PDX lines targeting Hypoxanthine-guanine phosphoribosyltransferase (HGPRT) and adenine phosphoribosyltransferase (APRT), key enzymes of the salvage pathway as described above. If our hypothesis is correct then forcing cells to use salvage pathway should sensitize GBM cells to alkylating-based chemotherapies.

2.c. To investigate the regulation of purine biosynthesis via ARL13B-IMPDH2 interaction in the therapy-resistant glioma stem cell population: Our laboratory, along with others, have recently shown that therapeutic stress can promote cellular plasticity-mediated stemness and shift the intertumoral fate equilibrium towards a more therapy resistant cancer stem cell-like state[49, 68-70]. We proposed that chemotherapy-induced cellular plasticity can increase the glioma stem cell (GSC)-like population, and may be responsible for resistance and disease recurrence. Moreover, the Rich group has recently demonstrated that GSCs preferentially utilize the de novo biosynthesis pathway to support their nucleotide demand[12]. Based on this, we are proposing that the ARL13b-IMPDH2 interaction regulates de novo purine biosynthesis pathway may play a role in promoting chemoresistance in GSC subpopulation. To investigate this hypothesis we will utilize 10 different GSC and matched-paired-differentiated GBM cell lines (DGC) and examine the following: i) ARL13B expression analysis by immunoblot, ii) ARL13B-IMPDH2 interaction difference between GSC and DGC state by IP, iii) role of ARL13B in maintenance of stemness by tumorsphere formation assay[50], iv) role of ARL13B-IMPDH interaction in regulating purine biosynthesis pathway in GSC by creating gain-of-function and loss-of-function models and perform isotope tracing experiments, and most importantly v) investigate if the ARL13B-IMPDH interactions are necessary for GSCs to promote chemoresistance by cell viability and tumorsphere formation assay; and finally, vi) in vivo tumor engraftment and TMZ sensitivity experiments according to our published protocol[49, 50]. These data will shed light on the mechanisms of chemoresistance in GSCs.

Figure 5D:
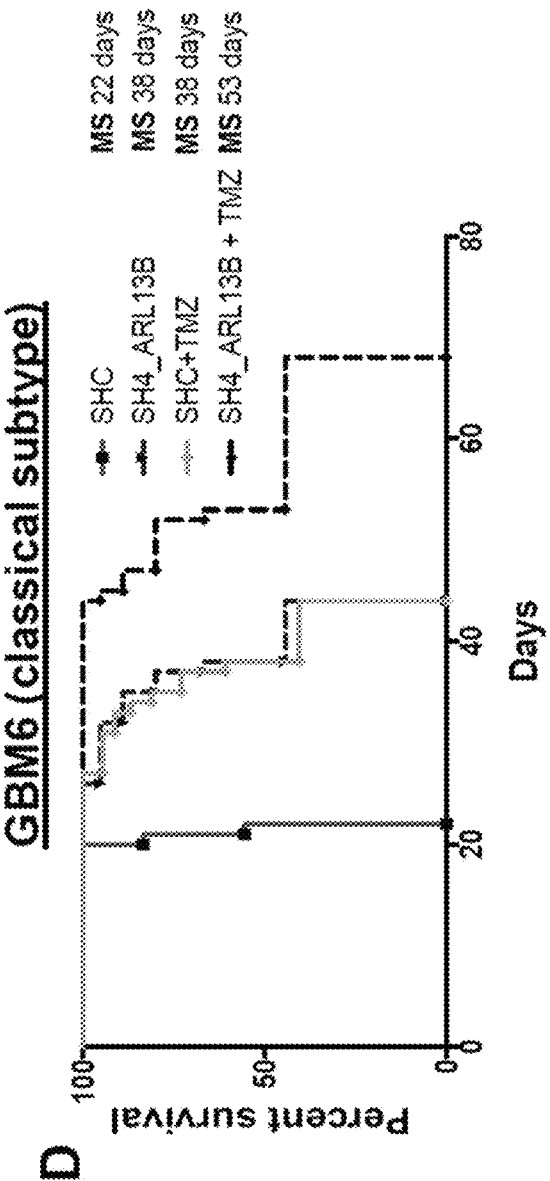

Data collection, analysis, statistical analysis, and power considerations: Most of the data collection and analysis will be performed as described in Aim 1. The primary endpoints the in vivo experiments in 2.c will be the overall survival. There will be 12 groups of animal vehicle control and TMZ (2.5 mg/kg), the same treatment for the gain of function and loss of function ARL13B respectively. We will implant 100 and 500 GSCs for each different group. The sample size calculation on survival analysis was currently done for two groups. We combined control and ARL13B loss-of-function (FIGS. 2 & 5). With n=11 animals per group, we will have 80% power to detect the effect of the treatment group compared with the control group based on a hazard ratio of 0.4 and our preliminary data (Data not shown). A Kaplan-Meier survival curve will be generated, and the log-rank test will be used to assess the therapeutic efficacy on animal survival.

Anticipated results and interpretation: Based on our preliminary data as well as published data[65] we expect to see that free alkylated nucleotides can be salvaged in GBM cells. This could be the cause of the observed enhanced DNA damage during TMZ therapy, however, as it has never been reported in the literature if alkylated purines can be salvaged and thus our experiments with O6mG would be critical to proof that. Finally, elucidating the mode of purine biosynthesis in the therapy-resistant GSC population and investigating the mechanisms of such regulation will provide new insight into the chemoresistance properties of GSCs.

Potential Pitfall Alternative Approaches: What if the post-TMZ therapy free alkylated nucleotides fail to be incorporated into the DNA via salvage pathway? In the event of DNA damage, the extracellular NAD pools can be depleted rapidly to support DNA damage response[71]. Based on this, one possible alternative mechanism could be NAD depletion, which may lead to inhibition of the de novo pathway and GBM cell proliferation. To test this, we will measure the intracellular NAD level during TMZ therapy (ab65348).

Summary: Together, these experiments will allow us examine the role of purine biosynthesis in promoting resistance to alkylating-based chemotherapy.

Aim 3: To Modulate the Purine Biosynthesis Pathway in Order to Overcome the Resistance Against the Alkylating Based Chemotherapy.

Rationale: Our preliminary data demonstrates that knocking out ARL13B significantly enhances the TMZ-induced DNA damage and therapeutic efficacy in the orthotopic PDX model. Based on this, we are proposing that the ARL13B-IMPDH2 regulated purine biosynthesis pathway may play a critical role in cellular adaptation to chemotherapy in GBM. In our final aim, we will first examine the intertumoral heterogeneity with respect to purine metabolism during TMZ therapy. Next, we will investigate if targeting purine biosynthesis can make GBM cells susceptible to alkylating-based chemotherapies and enhance the efficacy of the standard therapeutics.

Figures 9C, 9D:
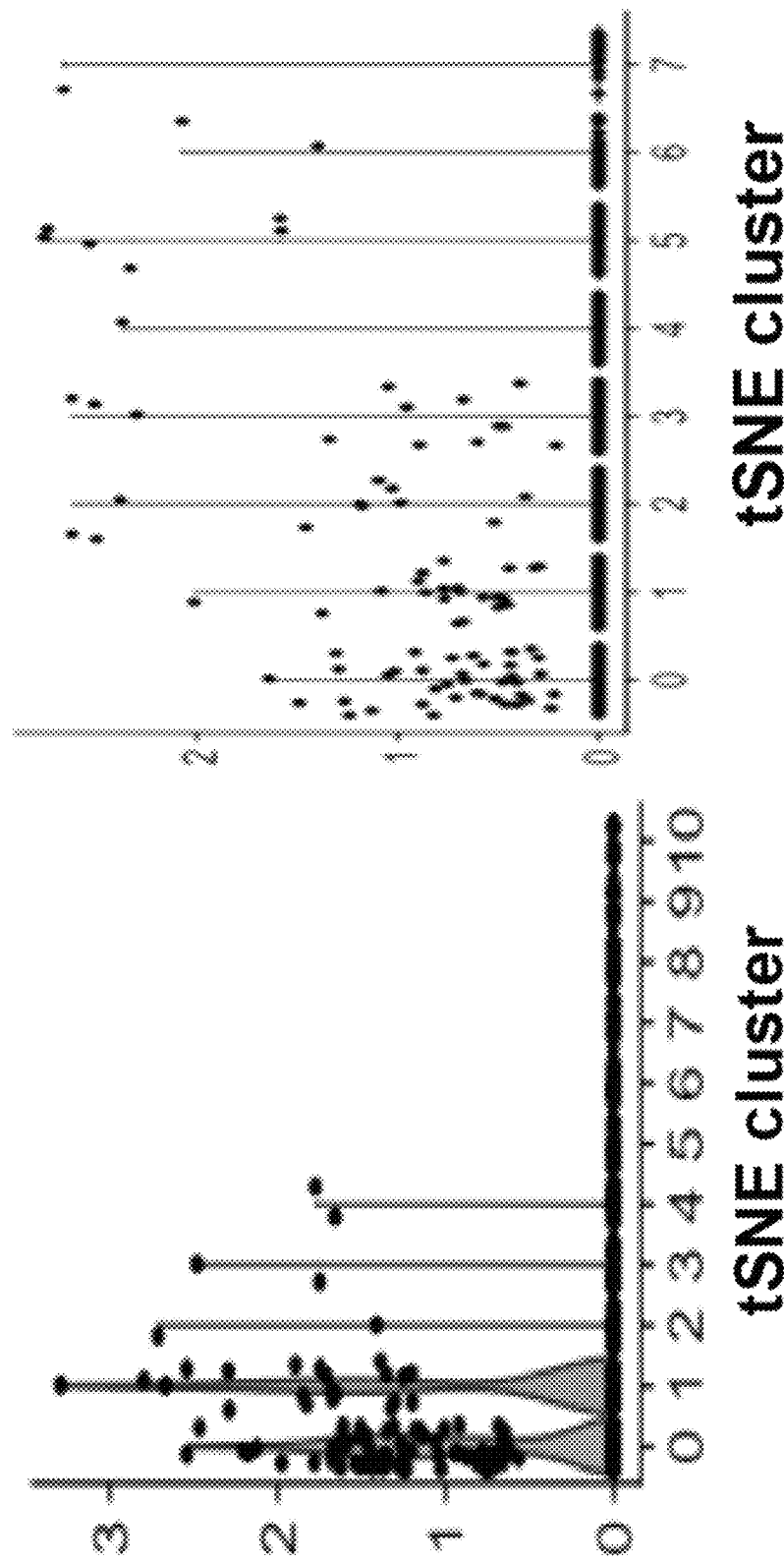

3.a. Elucidate the intratumor heterogeneity with respect to purine biosynthesis at the single cell resolution during TMZ therapy: GBM tissue contains multiple heterogeneous subpopulations of cells which thought to be a major driver of resistance and recurrence, and it is imperative that such heterogeneity should be accounted for when developing novel therapeutics[72]. Based on this, we set to examine the dynamics of in vivo intertumoral heterogeneity concerning purine biosynthesis by utilizing the Drop-Seq single-cell transcription analysis. A single cell suspension of orthotopic PDX GBM with different therapies will be created as described in section 1c and subject to single cell Drop-Seq analysis according to the published protocol[73]. Our initial data demonstrated the not only the intertumoral heterogeneity was enhanced post-therapy (FIG. 9, A vs. B), but also a new subpopulation with elevated ARL13B transcript show the highest activity of purine biosynthesis post-TMZ therapy (FIG. 9C, tSNE clusters 0 and 1). Based on this, we propose to molecularly characterize these subpopulations with hyperactive purine biosynthesis pathway to elucidate its role in chemoresistance. We have already established the experimental and analysis pipeline and intend to identify surface marker(s) to uniquely identify these populations via FACS and examine if their frequency will change during and post-therapy in the multiple PDX models. Such analysis will permit us to identify the molecular drivers for purine biosynthesis and may allow us to identify novel and actionable targets to prevent chemoresistance.

Figures 10A, 10B:
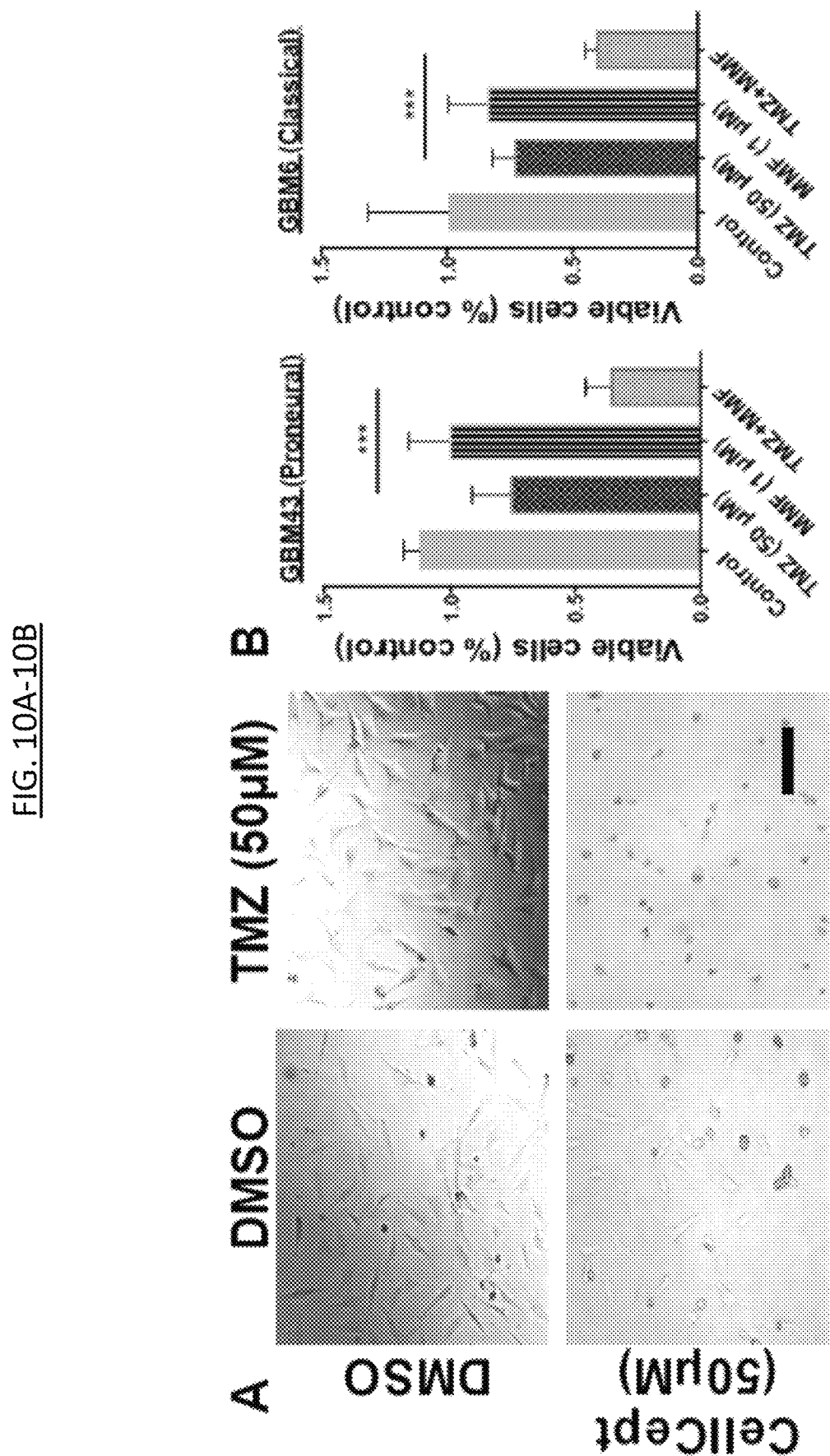
FIG. 10A-10C. IMPHD2 inhibitor CellCept sensitizes PDX GBM lines to TMZ therapy. A) Pictorial representation of cell viability post therapy. B) Cell viability measured by trypan blue exclusion method. C) Mice with orthotopic GBM43 treated with vehicle DMSO, TMZ 2.5 mg/kg for 5 days, MMF (20 mg/kg for 4 days and in combination and monitored by endpoint survival.
Figure 10C:
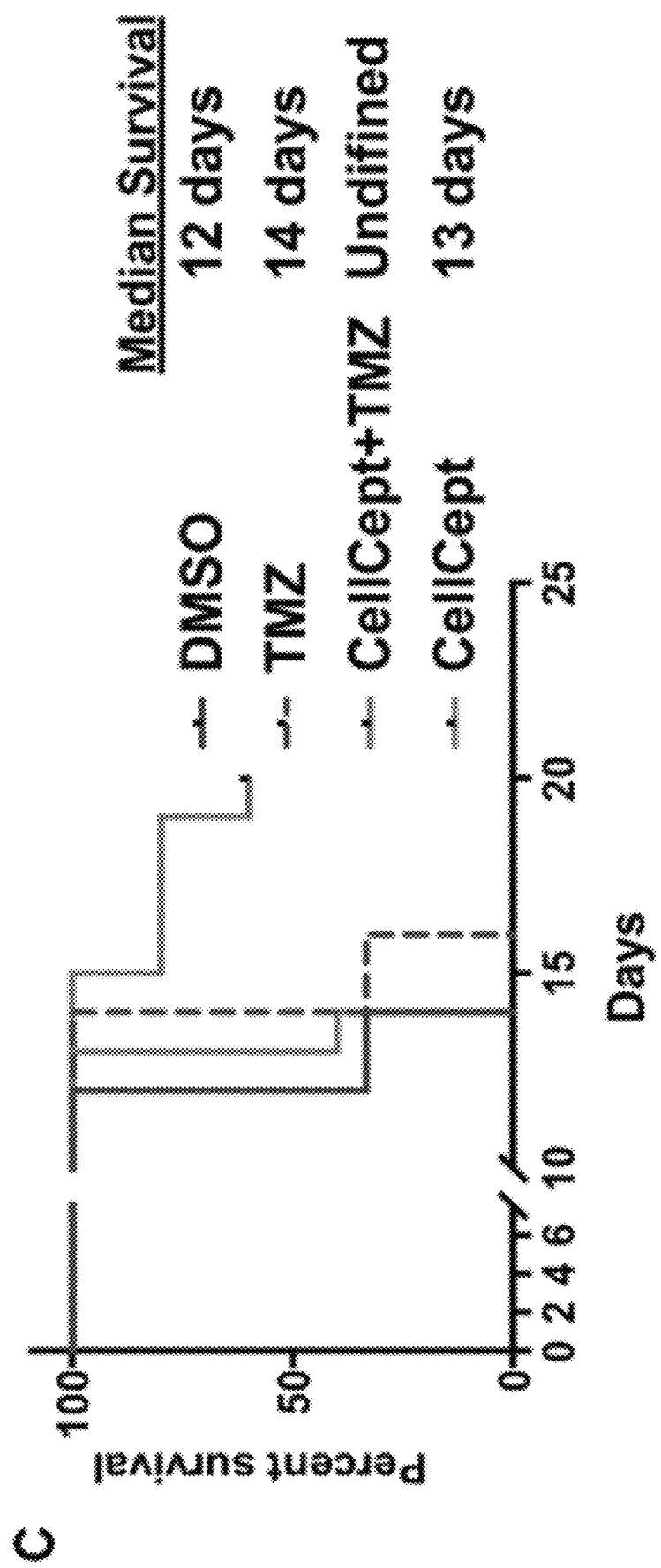

3.b. Evaluation of BBB permeable IMPDH inhibitor for anti-GBM activity: IMPDH is an extensively investigated molecular target for potential immunosuppressive, antiviral and anti-cancer chemotherapy[74]. Until now, two non-competitive and reversible inhibitors of IMPDH, CellCept and Myfortic, have been used clinically against autoimmunity[75]. Numerous studies have demonstrated the potential of this class of drugs as an anti-cancer agent and a number of phase I clinical trials with different cancers are ongoing[76, 77]. Among these drugs, CellCept demonstrated the ability to cross the blood-brain barrier (BBB) and promoted neuroprotection against various inflammatory conditions including EAE and stroke[68, 78]. Based on our preliminary data, we now seek to investigate if blocking the IMPDH-mediated de novo pathway will sensitize GBM cells towards alkylating chemotherapy such as TMZ and Carmustine (BCNU) both in vitro and in vivo. The initial evaluation convincingly demonstrated corporation between CellCept and TMZ in the PDX model (FIG. 10). We will next employ a panel of PDX GBM models that cover several variables (common genetic lesion: EGFR, PTEN mutation; MGMT promoter methylated and unmethylated; all three molecular subtypes; GSC vs. DGC models and sex) and evaluate the effect of IMPDH inhibitor alone or in combination with TMZ by i) the standard proliferation, cell cycle, apoptosis assay; ii) examine the extent of DNA damage measured as described in section 2.a; iii) estimating the IMPDH activity as well as the de novo and salvage pathway by tracing experiments as described in 1.c; iv) evaluate anti-glioma activity in the PDX model in vivo (3 models for each subtype). Orthotopically implanted PDX GBMs as well as mouse GBM GL261 and CT-2A in the immunocompetent host will be treated with DMSO (vehicle control), TMZ (2.5 mg/kg for five days), CellCept (dose TBD), or a combination of both drugs. Mice will be monitored by BLI for signs of tumor burden and will be sacrificed upon showing disease symptoms. A Kaplan-Meier survival curve will be generated to assess animal survival. Our preliminary data is very encouraging, and we believe that inhibiting the IMPDH activity and forcing the GBM cells to utilize the salvage pathway during chemotherapy will enhance the therapeutic efficacy of the standard care for GBM.

Data collection, analysis, statistical analysis, and power considerations: Most of the data collection and analysis will be performed at described in Aim 1 and Aim 2. There will be 12 groups of animal vehicle control and TMZ (2.5 mg/kg), MMF ((20-30 mg/kg) and combination for at least 3 subtypes of PDX. The samples size calculation on survival analysis was currently done for two groups. We combined control and ARL13B loss-of-function (FIG. 10). With n=11 animals per group, we will have 80% power to detect the effect of the treatment group compared with the control group based on a hazard ratio of 0.4 and our preliminary data (Data not shown). A Kaplan-Meier survival curve will be generated, and the log-rank test will be used to assess the therapeutic efficacy on animal survival.

Anticipated results and interpretation: Based on our preliminary data, we are extremely encouraged with our proposed hypothesis that by blocking de novo purine biosynthesis one can sensitize the GBM cells to alkylating based chemotherapy. We have a few FDA-approved BBB permeable drugs and are proposing to evaluate if they can enhance the therapeutic efficacy of TMZ-based chemotherapy.

Potential Pitfall Alternative Approaches: What if the IMPDH inhibitor CellCept fails to show activity against a specific subtype of GBM? We have another IMPDH inhibitor AVN944 which shows enhanced IMPDH activity as compared to CellCept[79, 80]. This drug is already in an clinical trial[81] and would be an excellent alternative for testing our proposed experiments).

Summary (Specific Aim 3): Collectively, these experiments will allow us to examine an novel druggable target to prevent the therapeutic resistance in GBM. Most importantly, we have few FDA approved drugs to evaluate and generate pre-clinical data for future clinical trial.

Timeline: The aims outlined above will address different aspects of the study concurrently, as shown on the right. The success of each aim does not depend on other aims, and as such, studies for multiple aims will be conducted in parallel.

In conclusion, our proposed studies will elucidate the molecular mechanisms of purine biosynthesis during alkylating-based chemotherapy and elucidate their role in GBM recurrence. These studies have direct translational relevance for a yet untreatable lethal disease.

REFERENCES

1. Anton K, Baehring J M, Mayer T. Glioblastoma multiforme: overview of current treatment and future perspectives. Hematol Oncol Clin North Am. 2012; 26(4): 825-53. PMID: 22794286.
2. Stupp R, Hegi M E, Mason W P, van den Bent M J, Taphoorn M J, Janzer R C, et al. Effects of radiotherapy with concomitant and adjuvant temozolomide versus radiotherapy alone on survival in glioblastoma in a randomised phase III study: 5-year analysis of the EORTC-NCIC trial. Lancet Oncol. 2009; 10(5): 459-66. PMID: 19269895.
3. Stupp R, Mason W P, van den Bent M J, Weller M, Fisher B, Taphoorn M J, et al. Radiotherapy plus concomitant and adjuvant temozolomide for glioblastoma. N Engl J Med. 2005; 352(10): 987-96. PMID: 15758009.
4. Hegi M E, Liu L, Herman J G, Stupp R, Wick W, Weller M, et al. Correlation of O6-methylguanine methyltransferase (MGMT) promoter methylation with clinical outcomes in glioblastoma and clinical strategies to modulate MGMT activity. J Clin Oncol. 2008; 26(25): 4189-99. PMID: 18757334.
5. Weber G, Prajda N. Targeted and non-targeted actions of anti-cancer drugs. Adv Enzyme Regul. 1994; 34: 71-89. PMID: 7942286.
6. Kinsella A R, Smith D, Pickard M. Resistance to chemotherapeutic antimetabolites: a function of salvage pathway involvement and cellular response to DNA damage. British journal of cancer. 1997; 75(7): 935-45. PMID: 9083327; PMCID: PMCPMC2222738.
7. Barfeld S J, Fazli L, Persson M, Marjavaara L, Urbanucci A, Kaukoniemi K M, et al. Myc-dependent purine biosynthesis affects nucleolar stress and therapy response in prostate cancer. Oncotarget. 2015; 6(14): 12587-602. PMID: 25869206; PMCID: PMCPMC4494960.
8. Goswami M T, Chen G, Chakravarthi B V, Pathi S S, Anand S K, Carskadon S L, et al. Role and regulation of coordinately expressed de novo purine biosynthetic enzymes PPAT and PAICS in lung cancer. Oncotarget. 2015; 6(27): 23445-61. PMID: 26140362; PMCID: PMCPMC4695129.
9. Rai B, Kaur J, Jacobs R, Anand S C. Adenosine deaminase in saliva as a diagnostic marker of squamous cell carcinoma of tongue. Clin Oral Investig. 2011; 15(3): 347-9. PMID: 20379753.
10. Dhankhar R, Dahiya K, Sharma T K, Ghalaut V S, Atri R, Kaushal V. Diagnostic significance of adenosine deaminase, uric acid and C-reactive protein levels in patients of head and neck carcinoma. Clin Lab. 2011; 57(9-10): 795-8. PMID: 22029199.

11. Pillwein K, Chiba P, Knoflach A, Czermak B, Schuchter K, Gersdorf E, et al. Purine metabolism of human glioblastoma in vivo. Cancer research. 1990; 50(5): 1576-9. PMID: 2154328.
12. Wang X, Yang K, Xie Q, Wu Q, Mack S C, Shi Y, et al. Purine synthesis promotes maintenance of brain tumor initiating cells in glioma. Nat Neurosci. 2017; 20(5): 661-73. PMID: 28346452; PMCID: PMCPMC6015494.
13. Eugui E M, Mirkovich A, Allison A C. Lymphocyte-selective antiproliferative and immunosuppressive effects of mycophenolic acid in mice. Scand J Immunol. 1991; 33(2): 175-83. PMID: 2017655.
14. Allison A C, Eugui E M. Mycophenolate mofetil and its mechanisms of action. Immunopharmacology. 2000; 47(2-3): 85-118. PMID: 10878285.
15. Ostrom Q T, Gittleman H, Liao P, Vecchione-Koval T, Wolinsky Y, Kruchko C, et al. CBTRUS Statistical Report: Primary brain and other central nervous system tumors diagnosed in the United States in 2010-2014. Neuro Oncol. 2017; 19(suppl 5): v1-v88. PMID: 29117289; PMCID: PMCPMC5693142.
16. Stupp R, Taillibert S, Kanner A, Read W, Steinberg D, Lhermitte B, et al. Effect of Tumor-Treating Fields Plus Maintenance Temozolomide vs Maintenance Temozolomide Alone on Survival in Patients With Glioblastoma: A Randomized Clinical Trial. JAMA. 2017; 318(23): 2306-16. PMID: 29260225; PMCID: PMCPMC5820703.
17. Cahill D P, Levine K K, Betensky R A, Codd P J, Romany C A, Reavie L B, et al. Loss of the mismatch repair protein MSH6 in human glioblastomas is associated with tumor progression during temozolomide treatment. Clinical cancer research: an official journal of the American Association for Cancer Research. 2007; 13(7): 2038-45. PMID: 17404084; PMCID: PMCPMC2873832.
18. Hombach-Klonisch S, Mehrpour M, Shojaei S, Harlos C, Pitz M, Hamai A, et al. Glioblastoma and chemoresistance to alkylating agents: Involvement of apoptosis, autophagy, and unfolded protein response. Pharmacol Ther. 2018; 184: 13-41. PMID: 29080702.
19. Yin J, Ren W, Huang X, Deng J, Li T, Yin Y. Potential Mechanisms Connecting Purine Metabolism and Cancer Therapy. Front Immunol. 2018; 9: 1697. PMID: 30105018; PMCID: PMCPMC6077182.
20. Sutani T, Sakata T, Nakato R, Masuda K, Ishibashi M, Yamashita D, et al. Condensin targets and reduces unwound DNA structures associated with transcription in mitotic chromosome condensation. Nat Commun. 2015; 6: 7815. PMID: 26204128; PMCID: PMCPMC4525155.
21. Suva M L, Rheinbay E, Gillespie S M, Patel A P, Wakimoto H, Rabkin S D, et al. Reconstructing and reprogramming the tumor-propagating potential of glioblastoma stem-like cells. Cell. 2014; 157(3): 580-94. PMID: 24726434; PMCID: PMCPMC4004670.
22. Sparmann A, van Lohuizen M. Polycomb silencers control cell fate, development and cancer. Nat Rev Cancer. 2006; 6(11): 846-56. PMID: 17060944.
23. Ezhkova E, Pasolli H A, Parker J S, Stokes N, Su I H, Hannon G, et al. Ezh2 orchestrates gene expression for the stepwise differentiation of tissue-specific stem cells. Cell. 2009; 136(6): 1122-35. PMID: 19303854; PMCID: PMCPMC2716120.
24. Kim E, Kim M, Woo D H, Shin Y, Shin J, Chang N, et al. Phosphorylation of EZH2 activates STAT3 signaling via STAT3 methylation and promotes tumorigenicity of glioblastoma stem-like cells. Cancer Cell. 2013; 23(6): 839-52. PMID: 23684459; PMCID: PMCPMC4109796.
25. Kim S H, Joshi K, Ezhilarasan R, Myers T R, Siu J, Gu C, et al. EZH2 protects glioma stem cells from radiation-induced cell death in a MELK/FOXM1-dependent manner. Stem Cell Reports. 2015; 4(2): 226-38. PMID: 25601206; PMCID: PMCPMC4325196.
26. Jin X, Kim L J Y, Wu Q, Wallace L C, Prager B C, Sanvoranart T, et al. Targeting glioma stem cells through combined BMI1 and EZH2 inhibition. Nat Med. 2017; 23(11): 1352-61. PMID: 29035367; PMCID: PMCPMC5679732.
27. Rosso L, Brock C S, Gallo J M, Saleem A, Price P M, Turkheimer F E, et al. A new model for prediction of drug distribution in tumor and normal tissues: pharmacokinetics of temozolomide in glioma patients. Cancer research. 2009; 69(1): 120-7. PMID: 19117994.
28. Beier D, Rohrl S, Pillai D R, Schwarz S, Kunz-Schughart L A, Leukel P, et al. Temozolomide preferentially depletes cancer stem cells in glioblastoma. Cancer research. 2008; 68(14): 5706-15. PMID: 18632623.
29. Brada M, Judson I, Beale P, Moore S, Reidenberg P, Statkevich P, et al. Phase I dose-escalation and pharmacokinetic study of temozolomide (SCH 52365) for refractory or relapsing malignancies. British journal of cancer. 1999; 81(6): 1022-30. PMID: 10576660; PMCID: PMC2362937.
30. Xu K, Wu Z J, Groner A C, He H H, Cai C, Lis R T, et al. EZH2 oncogenic activity in castration-resistant prostate cancer cells is Polycomb-independent. Science. 2012; 338(6113): 1465-9. PMID: 23239736; PMCID: PMCPMC3625962.
31. Lee S T, Li Z, Wu Z, Aau M, Guan P, Karuturi R K, et al. Context-specific regulation of NF-kappaB target gene expression by EZH2 in breast cancers. Mol Cell. 2011; 43(5): 798-810. PMID: 21884980.
32. Zhang Q, Hu J, Ling K. Molecular views of Arf-like small GTPases in cilia and ciliopathies. Exp Cell Res. 2013; 319(15): 2316-22. PMID: 23548655; PMCID: PMCPMC3742637.
33. Bay S N, Long A B, Caspary T. Disruption of the ciliary GTPase Arl13b suppresses Sonic hedgehog overactivation and inhibits medulloblastoma formation. Proc Natl Acad Sci USA. 2018; 115(7): 1570-5. PMID: 29378965; PMCID: PMCPMC5816136.
34. Sarkisian M R, Siebzehnrubl D, Hoang-Minh L, Deleyrolle L, Silver D J, Siebzehnrubl F A, et al. Detection of primary cilia in human glioblastoma. J Neurooncol. 2014; 117(1): 15-24. PMID: 24510433; PMCID: PMCPMC4433742.
35. Munoz J L, Rodriguez-Cruz V, Walker N D, Greco S J, Rameshwar P. Temozolomide resistance and tumor recurrence: Halting the Hedgehog. Cancer Cell Microenviron. 2015; 2(2). PMID: 27158638; PMCID: PMCPMC4856152.
36. Hedstrom L. IMP dehydrogenase: structure, mechanism, and inhibition. Chem Rev. 2009; 109(7): 2903-28. PMID: 19480389; PMCID: PMCPMC2737513.
37. Bell S, Kolobova I, Crapper L, Ernst C. Lesch-Nyhan Syndrome: Models, Theories, and Therapies. Mol Syndromol. 2016; 7(6): 302-11. PMID: 27920633; PMCID: PMCPMC5131334.
38. Liu Y, Bohn S A, Sherley J L. Inosine-5'-monophosphate dehydrogenase is a rate-determining factor for p53-dependent growth regulation. Mol Biol Cell. 1998; 9(1): 15-28. PMID: 9436988; PMCID: PMCPMC25212.
39. Ben-Sahra I, Hoxhaj G, Ricoult S J H, Asara J M, Manning B D. mTORC1 induces purine synthesis through control of the mitochondrial tetrahydrofolate cycle. Science. 2016; 351(6274): 728-33. PMID: 26912861; PMCID: PMCPMC4786372.
40. Carlson B L, Grogan P T, Mladek A C, Schroeder M A, Kitange G J, Decker P A, et al. Radiosensitizing effects of temozolomide observed in vivo only in a subset of O6-methylguanine-DNA methyltransferase methylated glioblastoma multiforme xenografts. Int J Radiat Oncol Biol Phys. 2009; 75(1): 212-9. PMID: 19695438; PMCID: PMCPMC2773462.
41. Phillips H S, Kharbanda S, Chen R, Forrest W F, Soriano R H, Wu T D, et al. Molecular subclasses of high-grade glioma predict prognosis, delineate a pattern of disease progression, and resemble stages in neurogenesis. Cancer Cell. 2006; 9(3): 157-73. PMID: 16530701.
42. Wen P Y, Kesari S. Malignant gliomas in adults. N Engl J Med. 2008; 359(5): 492-507. PMID: 18669428.
43. Garrido W, Rocha J D, Jaramillo C, Fernandez K, Oyarzun C, San Martin R, et al. Chemoresistance in high-grade gliomas: relevance of adenosine signalling in stem-like cells of glioblastoma multiforme. Curr Drug Targets. 2014; 15(10): 931-42. PMID: 25174341.
44. Liao L X, Song X M, Wang L C, Lv H N, Chen J F, Liu D, et al. Highly selective inhibition of IMPDH2 provides the basis of antineuroinflammation therapy. Proc Natl Acad Sci USA. 2017; 114(29): E5986-E94. PMID: 28674004; PMCID: PMCPMC5530702.
45. Keppeke G D, Calise S J, Chan E K, Andrade L E. Anti-rods/rings autoantibody generation in hepatitis C patients during interferon-alpha/ribavirin therapy. World J Gastroenterol. 2016; 22(6): 1966-74. PMID: 26877604; PMCID: PMCPMC4726672.
46. Tsipotis E, Gupta N R, Raman G, Zintzaras E, Jaber B L. Bioavailability, Efficacy and Safety of Generic Immunosuppressive Drugs for Kidney Transplantation: A Systematic Review and Meta-Analysis. Am J Nephrol. 2016; 44(3): 206-18. PMID: 27576318.
47. Esteller M, Garcia-Foncillas J, Andion E, Goodman S N, Hidalgo O F, Vanaclocha V, et al. Inactivation of the DNA-repair gene MGMT and the clinical response of gliomas to alkylating agents. N Engl J Med. 2000; 343 (19): 1350-4. PMID: 11070098.
48. Giannini C, Sarkaria J N, Saito A, Uhm J H, Galanis E, Carlson B L, et al. Patient tumor EGFR and PDGFRA gene amplifications retained in an invasive intracranial xenograft model of glioblastoma multiforme. Neuro Oncol. 2005; 7(2): 164-76. PMID: 15831234; PMCID: PMCPMC1871885.
49. Auffinger B, Tobias A L, Han Y, Lee G, Guo D, Dey M, et al. Conversion of differentiated cancer cells into cancer stem-like cells in a glioblastoma model after primary chemotherapy. Cell Death Differ. 2014; 21(7): 1119-31. PMID: 24608791.
50. Lee G, Auffinger B, Guo D, Hasan T, Deheeger M, Tobias A L, et al. Dedifferentiation of Glioma Cells to Glioma Stem-like Cells By Therapeutic Stress-induced HIF Signaling in the Recurrent GBM Model. Mol Cancer Ther. 2016; 15(12): 3064-76. PMID: 27765847; PMCID: PMCPMC5298928.
51. Guvenc H, Pavlyukov M S, Joshi K, Kurt H, Banasavadi-Siddegowda Y K, Mao P, et al. Impairment of glioma stem cell survival and growth by a novel inhibitor for Survivin-Ran protein complex. Clinical cancer research: an official journal of the American Association for Cancer Research. 2013; 19(3): 631-42. PMID: 23251006; PMCID: PMCPMC4295559.
52. McDonnell J M. Surface plasmon resonance: towards an understanding of the mechanisms of biological molecular recognition. Curr Opin Chem Biol. 2001; 5(5): 572-7. PMID: 11578932.
53. He M, Bianchi M E, Coleman T R, Tracey K J, Al-Abed Y. Exploring the biological functional mechanism of the HMGB1/TLR4/MD-2 complex by surface plasmon resonance. Mol Med. 2018; 24(1): 21. PMID: 30134799; PMCID: PMCPMC6085627.
54. Natsumeda Y, Ohno S, Kawasaki H, Konno Y, Weber G, Suzuki K. Two distinct cDNAs for human IMP dehydrogenase. J Biol Chem. 1990; 265(9): 5292-5. PMID: 1969416.
55. Ivanova A A, Caspary T, Seyfried N T, Duong D M, West A B, Liu Z, et al. Biochemical characterization of purified mammalian ARL13B protein indicates that it is an atypical GTPase and ARL3 guanine nucleotide exchange factor (GEF). J Biol Chem. 2017; 292(26): 11091-108. PMID: 28487361; PMCID: PMCPMC549179.
56. Ben-Sahra I, Howell J J, Asara J M, Manning B D. Stimulation of de novo pyrimidine synthesis by growth signaling through mTOR and S6K1. Science. 2013; 339 (6125): 1323-8. PMID: 23429703; PMCID: PMCPMC3753690.
57. Huang F, Ni M, Chalishazar M D, Huffman K E, Kim J, Cai L, et al. Inosine Monophosphate Dehydrogenase Dependence in a Subset of Small Cell Lung Cancers. Cell Metab. 2018; 28(3): 369-82 e5. PMID: 30043754; PMCID: PMCPMC6125205.
58. Marsh D J, Weingarth D T, Novi D E, Chen H Y, Trumbauer M E, Chen A S, et al. Melanin-concentrating hormone 1 receptor-deficient mice are lean, hyperactive, and hyperphagic and have altered metabolism. Proc Natl Acad Sci USA. 2002; 99(5): 3240-5. PMID: 11867747; PMCID: PMCPMC122503.
59. Yamada M, Chiba T, Sasabe J, Nawa M, Tajima H, Niikura T, et al. Implanted cannula-mediated repetitive administration of Abeta25-35 into the mouse cerebral ventricle effectively impairs spatial working memory. Behav Brain Res. 2005; 164(2): 139-46. PMID: 16122819.
60. Nemkov T, Sun K, Reisz J A, Song A, Yoshida T, Dunham A, et al. Hypoxia modulates the purine salvage pathway and decreases red blood cell and supernatant levels of hypoxanthine during refrigerated storage. Haematologica. 2018; 103(2): 361-72. PMID: 29079593; PMCID: PMCPMC5792281.
61. Bhat K P L, Balasubramaniyan V, Vaillant B, Ezhilarasan R, Hummelink K, Hollingsworth F, et al. Mesenchymal differentiation mediated by NF-kappaB promotes radiation resistance in glioblastoma. Cancer Cell. 2013; 24(3): 331-46. PMID: 23993863; PMCID: PMCPMC3817560.
62. Annovazzi L, Mellai M, Schiffer D. Chemotherapeutic Drugs: DNA Damage and Repair in Glioblastoma. Cancers (Basel). 2017; 9(6). PMID: 28587121; PMCID: PMCPMC5483876.
63. Ipata P L, Camici M, Micheli V, Tozz M G. Metabolic network of nucleosides in the brain. Curr Top Med Chem. 2011; 11(8): 909-22. PMID: 21401502.
64. Fasullo M, Endres L. Nucleotide salvage deficiencies, DNA damage and neurodegeneration. Int J Mol Sci. 2015; 16(5): 9431-49. PMID: 25923076; PMCID: PMCPMC4463597.
65. Berg J M T J, Stryer L. Purine Bases Can Be Synthesized de Novo or Recycled by Salvage Pathways. Biochemistry 5th edition. 2002; 5th edition: Section 25.2.

66. Zauri M, Berridge G, Thezenas M L, Pugh K M, Goldin R, Kessler B M, et al. CDA directs metabolism of epigenetic nucleosides revealing a therapeutic window in cancer. Nature. 2015; 524(7563): 114-8. PMID: 26200337; PMCID: PMCPMC4866471.

67. Vilpo J A, Vilpo L M. Nucleoside monophosphate kinase may be the key enzyme preventing salvage of DNA 5-methylcytosine. Mutat Res. 1993; 286(2): 217-20. PMID: 7681533.

68. Dahan P, Martinez Gala J, Delmas C, Monferran S, Malric L, Zentkowski D, et al. Ionizing radiations sustain glioblastoma cell dedifferentiation to a stem-like phenotype through survivin: possible involvement in radioresistance. Cell death & disease. 2014; 5: e1543. PMID: 25429620; PMCID: PMC4260760.

69. O'Brien-Ball C, Biddle A. Reprogramming to developmental plasticity in cancer stem cells. Dev Biol. 2017; 430(2): 266-74. PMID: 28774727.

70. Chaffer C L, Brueckmann I, Scheel C, Kaestli A J, Wiggins P A, Rodrigues L O, et al. Normal and neoplastic nonstem cells can spontaneously convert to a stem-like state. Proc Natl Acad Sci USA. 2011; 108(19): 7950-5. PMID: 21498687; PMCID: PMCPMC3093533.

71. Cohen A, Barankiewicz J. Metabolic consequences of DNA damage: alteration in purine metabolism following poly(ADP ribosyl)ation in human T-lymphoblasts. Arch Biochem Biophys. 1987; 258(2): 498-503. PMID: 2960266.

72. Meyer M, Reimand J, Lan X, Head R, Zhu X, Kushida M, et al. Single cell-derived clonal analysis of human glioblastoma links functional and genomic heterogeneity. Proc Natl Acad Sci USA. 2015; 112(3): 851-6. PMID: 25561528; PMCID: PMCPMC4311802.

73. Macosko E Z, Basu A, Satija R, Nemesh J, Shekhar K, Goldman M, et al. Highly Parallel Genome-wide Expression Profiling of Individual Cells Using Nanoliter Droplets. Cell. 2015; 161(5): 1202-14. PMID: 26000488; PMCID: PMCPMC4481139.

74. Braun-Sand S B, Peetz M. Inosine monophosphate dehydrogenase as a target for antiviral, anticancer, antimicrobial and immunosuppressive therapeutics. Future Med Chem. 2010; 2(1): 81-92. PMID: 21426047.

75. Siebert A, Prejs M, Cholewinski G, Dzierzbicka K. New Analogues of Mycophenolic Acid. Mini Rev Med Chem. 2017; 17(9): 734-45. PMID: 27903231.

76. Rodriguez-Pascual J, Sha P, Garcia-Garcia E, Rajeshkumar N V, De Vicente E, Quijano Y, et al. A preclinical and clinical study of mycophenolate mofetil in pancreatic cancer. Invest New Drugs. 2013; 31(1): 14-9. PMID: 22669334.

77. Takebe N, Cheng X, Wu S, Bauer K, Goloubeva O G, Fenton R G, et al. Phase I clinical trial of the inosine monophosphate dehydrogenase inhibitor mycophenolate mofetil (cellcept) in advanced multiple myeloma patients. Clinical cancer research: an official journal of the American Association for Cancer Research. 2004; 10(24): 8301-8. PMID: 15623606.

78. Zhu Z, You W, Xie Z, Wang P, Liu Z, Wang C, et al. Mycophenolate mofetil improves neurological function and alters blood T-lymphocyte subsets in rats with experimental autoimmune encephalomyelitis. J Int Med Res. 2014; 42(2): 530-41. PMID: 24496150.

79. Chen L, Pankiewicz K W. Recent development of IMP dehydrogenase inhibitors for the treatment of cancer. Curr Opin Drug Discov Devel. 2007; 10(4): 403-12. PMID: 17659481.

80. Huang M, Ji Y, Itahana K, Zhang Y, Mitchell B. Guanine nucleotide depletion inhibits pre-ribosomal RNA synthesis and causes nucleolar disruption. Leuk Res. 2008; 32(1): 131-41. PMID: 17462731; PMCID: PMCPMC4552191.

81. Hamilton J M, Harding M W, Genna T, Bol D K. A phase I dose-ranging study of the pharmacokinetics, pharmacodynamics, safety, and tolerability of AVN944, an IMPDH inhibitor, in healthy male volunteers. J Clin Pharmacol. 2009; 49(1): 30-8. PMID: 18971325.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method of treating a proliferative cell disease or disorder in a subject in need thereof, the method comprising:
   (a) administering to the subject a therapeutic agent that inhibits or reduces the biological activity of inosine-5'-monophosphate dehydrogenase 1 (IMDPH1) or inosine-5'-monophosphate dehydrogenase 2 (IMDPH2); and
   (b) administering to the subject an alkylating agent,
   wherein the therapeutic agent that inhibits or reduces the biological activity of IMDPH1 or IMDPH2 is selected from the group consisting of mizoribine, tiazofurin, mycophenolic mofetil, and mycophenolic acid.

2. The method of claim 1, wherein the therapeutic agent that inhibits or reduces the biological activity of IMDPH1 or IMDPH2 is mycophenolic mofetil.

3. The method of claim 1, wherein the therapeutic that inhibits or reduces the biological activity of IMDPH1 or IMDPH2 is selected from mizoribine, mycophenolic mofetil, or mycophenolic acid.

4. The method of claim 1, wherein the alkylating agent is selected from the group consisting of triazenes, nitrogen mustards, nitrosoureas, alkyl sulfates, and ethylenimines.

5. The method of claim 1, wherein the alkylating agent is 3,4-dihydro-3-methyl-4-oxoimidazo[5,1-d]-1,2,3,5-tetrazine-8-carboxamide otherwise known as temozolomide.

6. The method of claim 1, wherein the proliferative cell disease or disorder is a glioblastoma.

7. The method of claim 1, wherein the proliferative cell disease or disorder is an astrocytoma.

8. The method of claim 1, wherein the therapeutic agent that inhibits or reduces the biological activity of IMDPH1 or IMDPH2 is administered to the subject prior to the alkylating agent.

* * * * *